US007524648B2

(12) United States Patent
Chen et al.

(10) Patent No.: US 7,524,648 B2
(45) Date of Patent: Apr. 28, 2009

(54) EXPRESSION SYSTEM FOR ENHANCING SOLUBILITY AND IMMUNOGENEICITY OF RECOMBINANT PROTEINS

(75) Inventors: Ming-Yu Chen, Miaoli (TW); Chin-Kai Chuang, Hsinchu (TW); Yu-Hsyu Su, Miaoli (TW); Chiu-Ting Fan, Hsinchu County (TW); Jung-Chuan Yu, Hsinchu (TW); Wen-Chuan Lee, Hsinchu (TW)

(73) Assignees: Stresspro Biomedicine Incorporation, Hsinchu (TW); Animal Technology Institute Taiwan, Miaoli Hsien (TW)

( * ) Notice: Subject to any disclaimer, the term of this patent is extended or adjusted under 35 U.S.C. 154(b) by 0 days.

(21) Appl. No.: 12/149,606

(22) Filed: May 5, 2008

(65) Prior Publication Data

US 2008/0274508 A1 Nov. 6, 2008

(30) Foreign Application Priority Data

May 4, 2007 (TW) .............................. 96115989 A

(51) Int. Cl.
*C12P 21/06* (2006.01)
*C12N 15/00* (2006.01)
*C12N 1/20* (2006.01)
*C07H 21/04* (2006.01)

(52) U.S. Cl. ................ 435/69.1; 435/320.1; 435/252.3; 536/23.1

(58) Field of Classification Search ................ 435/69.1, 435/252.3, 320.1; 536/23.1
See application file for complete search history.

(56) References Cited

OTHER PUBLICATIONS

Hennessy et al., "Not all J domains are created equal: Implications for the specificity of Hsp40-Hsp70 interactions", Protein Sci. 14, pp. 1697-1709, (2005).

Walsh et al., "The J-protein family: modulating protein assembly,disassembly and translocation", EMBO reports, vol. 5, No. 6, pp. 567-571, (2004).

Jo Rg Reimann and Reinhold Schirmbeck, "DNA vaccines expressing antigenswith a stress protein-capturing domain display enhanced immunogenicity", Immunological Reviews, vol. 199, pp. 54-67, (2004).

Greene et al., "Role of the J-domain in the cooperation of Hsp40 with Hsp70", PNAS USA vol. 95, pp. 6108-6113, (1998).

Tilstra et al., "Protein transduction: identification, characterization and optimization", Biochemical Society Transactions, vol. 35, part 4, pp. 811-815, (2007).

Qiu et al., "The diversity of the DnaJ/Hsp40 family, the crucial partners for Hsp70 chaperones", Cell. Mol. Life Sci. 63, pp. 2560-2570, (2006).

Yichen Lai et al., (2005) "Selectively increasing inducible heat shock protein 70 via TAT-protein transduction protects neurons from nitrosative stress and excitotoxicity" Journal of Neurochemistry, 2005, 94, 360-366.

*Primary Examiner*—Maryam Monshipouri
(74) *Attorney, Agent, or Firm*—Intellectual Property Connections, Inc.; Hsin-Ming Saunders

(57) ABSTRACT

Expression system for enhancing solubility and immunogenicity of recombinant proteins. The expression system includes a protein expression vector that contains a chimeric gene encoding a chimeric protein. The chimeric protein contains three polypeptidyl fragments: (a) a first polypeptidyl fragment at the N-terminal end of the chimeric protein that contains a protein transduction domain (PTD) or a fragment thereof having HIV Tat PTD activity; (b) a second polypeptidyl fragment at the C-terminal end of the first polypeptidyl fragment that contains a J-domain or a fragment thereof having heat shock protein 70 (Hsp70)-interacting activity; and (c) a third polypeptidyl fragment at the C-terminal end of the second polypeptidyl fragment that contains a target protein or polypeptide.

20 Claims, 15 Drawing Sheets pET22b-PTD$_1$

```
                             T7 primer
                         ------------------>
AGATCT CGATCCCCGCGAAAT TAATACGACTCACTAT AGG GGAATTGTGAGCGGATAACAATTCC CC TCTAGA AATAATTTTGTTTAAGA
BglII                     T7 promoter             lac operator                XbaI

               NdeI
AGGAG ATATA CAT ATG TAT GGT CGT AAG AAA CGT CGT CAG CGT CGT CGT
rbs             Met Tyr Gly Arg Lys Lys Arg Arg Gln Arg Arg Arg

BamHI   EcoRI    SacI     SalI    HindIII  NotI      XhoI
GGG ATC CG AAT TCG AGC TCC GTC GAC AAG CTT GCG GCC GCA CTC GAG
Gly Asp    Asn Ser Ser Ser Val Asp Lys Leu Ala Ala Ala Leu Glu

CAC CAC CAC CAC CAC CAC TGA GATCCGGCTGCTAACAAAGCCCGAAAGGAAGCTGAGTTGGCTGCTGCCACCGCTGAGCAATAA
His His His His His His stop
       His-tag

CTAGCATAACCCCTTGGGGCCTCTAAACGGGTCTTGAGGGGTTTTTTG
             T7 terminator
```

FIG. 2A pET22b-PTD1-J1

T7 primer →

AGATCT CGATCCCCGCGAAAT TAATACGACTCACTAT AGG GGAATTGTGAGCGGATAACAATTCC CC TCTAGA AATAATTTTGTTTAAGA
*Bgl*II T7 promoter lac operator *Xba*I

*Nde*I
AGGAG ATATA CAT ATG TAT GGT CGT AAG AAA CGT CGT CAG CGT CGT CGT
rbs Met Tyr Gly Arg Lys Lys Arg Arg Gln Arg Arg Arg

*Bam*HI
GGG ATC CTG GGT AAA GAT TAC TAC CAG ACT CAC GGT CTC GCT CGT GGT GCA TCT GAT GAT GAA ATC AAA CGT GCT TAC CGT CGT CAG GCA CTG CGT TAC
Gly Asp Leu Gly Lys Asp Tyr Tyr Gln Thr Leu Gly Leu Ala Arg Gly Ala Ser Asp Asp Glu Ile Lys Arg Ala Tyr Arg Arg Gln Ala Leu Arg Tyr

CAT CCA GAC AAA AAC AAA GAA CCG CGT GCA GAA GAG AAA TTC AAA GAG ATC GCA GAA GCA TAC GAC GTT CTG AGC GAT CCA CGT AAA CGT GAA ATC TCC
His Pro Asp Lys Asn Lys Glu Pro Arg Ala Glu Glu Lys Phe Lys Glu Ile Ala Glu Ala Tyr Asp Val Leu Ser Asp Pro Arg Lys Arg Lys Arg Glu Ile Phe

GAC CGT TAC GGT GAA GAA GGT CTG AAA GGT GGT TCT GGT GGT GC
Asp Arg Tyr Gly Glu Glu Gly Leu Lys Gly Gly Ser Gly Gly Ala

*Eco*RI *Sac*I *Sal*I *Hind*III *Not*I *Xho*I
G AAT TCG AGC TCC GTC GAC AAG CTT GCG GCC GCA CTC GAG
Asn Ser Ser Ser Val Asp Lys Leu Ala Ala Ala Leu Glu CAC CAC CAC CAC CAC CAC TGA GATCCGGCTGCTAACAAAGCCCGAAAGGAAGCTGAGTTGGCTGCTGCCACCGCTGAGCAATAA
His His His His His His stop
His-tag

CTAGCATAACCCCTTGGGGCCTCTAAACGGGTCTTGAGGGGTTTTTTG
T7 terminator

FIG. 2B

| IPTG Induction Period (hr) | 1 | 2 | 3 | 4 | 5 | 6 | 16 |
|---|---|---|---|---|---|---|---|
| Recombinant Protein / Total Proteins (% w/w) | 65 | 85 | 89 | 91 | 92 | 92 | 77 |

| IPTG Induction Period (hr) | 1 | 2 | 3 | 4 | 5 | 6 | 16 |
|---|---|---|---|---|---|---|---|
| Recombinant Protein / Total Proteins (% w/w) | 27 | 45 | 37 | 54 | 51 | 46 | 10 |

| IPTG Induction Period (hr) | 1 | 2 | 3 | 4 | 5 | 6 | 16 |
|---|---|---|---|---|---|---|---|
| Recombinant Protein / Total Proteins (% w/w) | 16 | 33 | 30 | 27 | 10 | - | - |

| IPTG Induction Period (hr) | 1 | 2 | 3 | 4 | 5 | 6 |
|---|---|---|---|---|---|---|
| Recombinant Protein / Total Proteins (% w/w) | 74 | 87 | 89 | 90 | 90 | 90 |

| IPTG Induction Period (hr) | 1 | 2 | 3 | 4 | 5 | 6 | 7 | 16 |
|---|---|---|---|---|---|---|---|---|
| Recombinant Protein / Total Proteins (% w/w) | 12 | 31 | 38 | 28 | 32 | 27 | 34 | 32 |

| IPTG Induction Period (hr) | 1 | 2 | 3 | 5 | 6 | 16 |
|---|---|---|---|---|---|---|
| Recombinant Protein / Total Proteins (% w/w) | 11 | 25 | 31 | 36 | 39 | - |

| IPTG Induction Period (hr) | 1 | 2 | 3 | 4 | 5 | 6 |
|---|---|---|---|---|---|---|
| Recombinant Protein / Total Proteins (% w/w) | 26 | 39 | 43 | 38 | 36 | 33 |

EXPRESSION SYSTEM FOR ENHANCING SOLUBILITY AND IMMUNOGENEICITY OF RECOMBINANT PROTEINS

FIELD OF THE INVENTION

The present invention relates generally to an expression system and more specifically to an expression system for recombinant proteins with enhanced solubility and immunogenicity.

BACKGROUND OF THE INVENTION

The demand for efficient and large scale production of therapeutic proteins is steadily increasing as more recombinant proteins are approved for use in humans. Using *E. coli* expression system for production of recombinant proteins, however, frequently results in formation of water-insoluble protein inclusion bodies, instead of functional, soluble proteins. Additionally, resolubilized proteins from inclusion bodies do not elicit as strong an immune responses in rats and mice as soluble, native protein does.

The Hsp70-peptide antigen complex plays an important role in the antigen presentation process (Mycko et al., 2004; Bendz et al., 2007). The molecular chaperone/co-chaperone pair (Hsp70/Hsp40) is highly conserved throughout evolution. Eukaryotic Hsp70 genes are descents of the bacterial DnaK gene. DnaK and HSP70 have over 50% homology in their amino acid sequences. The structure of DnaK/Hsp70 is composed of a N-terminal ATPase domain, a substrate binding domain, and a C-terminal lid domain (Genevaux et al., 2007; Shaner & Morano, 2007). Hsp40s represent a large protein family that functions to specify the cellular action of Hsp70 chaperone proteins. There are 44 members of Hsp40 genes found in human genome. Twelve of them are descents of *E. coli* DnaJ. Although their amino acid sequences outside the J-domain are divergent, the 75 amino acid J-domain of the Hsp40 proteins is highly conserved. The J-domain of Hsp40 interacts directly with the Hsp70 ATPase domain to enhance the ATP hydrolysis rate which in turn increases the substrate binding affinity. Hsp40 proteins also bind client substrate and deliver it to the Hsp70 (Fan et al., 2003).

Protein transduction domain (PTD) peptides are able to ferry large molecules into cells independent of classical endocytosis. They are used to enhance cellular uptake of drugs, proteins, polynucleotides and liposomes (Tilstra et al., 2007).

Neither the PTD nor the Hsp40 J-domain has been employed in the development of an expression system for improving solubility and immunogenicity of a recombinant protein. A previously unaddressed need exists in the art to address the aforementioned deficiencies and inadequacies, especially in connection with the development of an expression system for a recombinant protein with enhanced solubility and immunogenicity.

SUMMARY OF THE INVENTION

The invention is related to a protein expression vector for increasing the solubility of a target protein or polypeptide in a host cell expression system, and/or enhancing the immunogenicity of a target protein or polypeptide. The expression vector of the invention has superior performances in producing high yields of soluble recombinant proteins when compared to other commercially available *E. col.* expression vectors. In addition, the expression vector of the invention is capable of enhancing the immunogenicity of small peptides that by them-selves are weak in inducing antibodies in animals.

One aspect of the invention relates to a chimeric protein that contains three polypeptide fragments: (a) a first polypeptidyl fragment located at the N-terminal end of the chimeric protein that contains a protein transduction domain (PTD) or a fragment thereof having HIV Tat PTD activity; (b) a second polypeptidyl fragment located at the C-terminal end of the first polypeptidyl fragment that contains a J-domain or a fragment thereof having heat shock protein 70 (Hsp70)-interacting activity; and (c) a third polypeptidyl fragment at the C-terminal end of the second polypeptidyl fragment that contains a target protein or polypeptide.

Another aspect of the invention relates to a chimeric gene that includes three DNA sequences: (a) a first DNA sequence encoding a protein transduction domain (PTD) or a fragment thereof having HIV Tat PTD activity; (b) a second DNA sequence encoding, linked in translation frame with the first DNA sequence, encoding a J-domain or a fragment thereof having heat shock protein 70 (Hsp70)-interacting activity; and (c) a third DNA sequence encoding, linked in translation frame with the second DNA sequence, encoding a target protein or polypeptide.

Another aspect of the invention relates to a chimeric gene that comprises two DNA sequences: (a) a first DNA sequence encoding a protein transduction domain (PTD) or a fragment thereof having HIV Tat PTD activity; and (b) a second DNA sequence encoding, linked in translation frame with the first DNA sequence, encoding a J-domain or a fragment thereof having heat shock protein 70 (Hsp70)-interacting activity.

Further another aspect of the invention relates to a protein expression vector that comprises a chimeric gene as aforementioned. Yet another aspect of the invention relates to an isolated host cell that contains an expression vector having chimeric gene as aforementioned.

Another aspect of the invention relates to a method for enhancing immunogenicity and/or solubility of a target protein or polypeptide in a host cell expression system. The method includes the steps of: (a) generating a protein expression vector according to claim 18; (b) transfecting a host cell with the expression vector; (c) culturing the host cell transfected with the expression vector under conditions that permit expression of the target protein or polypeptide; and (d) isolating the target protein or polypeptide.

Further another aspect of the invention relates to a method of expressing a target protein or polypeptide. The method contains the steps of: (a) transfecting a host cell with the expression vector of claim 18; (b) culturing the host cell transfected with the expression vector under conditions that permit expression of the target protein or polypeptide; and (c) isolating the target protein or polypeptide.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention.

Wherever possible, the same reference numbers are used throughout the drawings to refer to the same or like elements of an embodiment.

BRIEF DESCRIPTION OF THE DRAWINGS

FIG. 2A shows the nucleotide sequence and the encoded amino acid sequence of the plasmid of FIG. 1A.

FIG. 2B shows the nucleotide sequence and the encoded amino acid sequence of the plasmid of FIG. 1B.

DETAILED DESCRIPTION OF THE INVENTION

Definitions

Figures 1A, 1B, 1C:
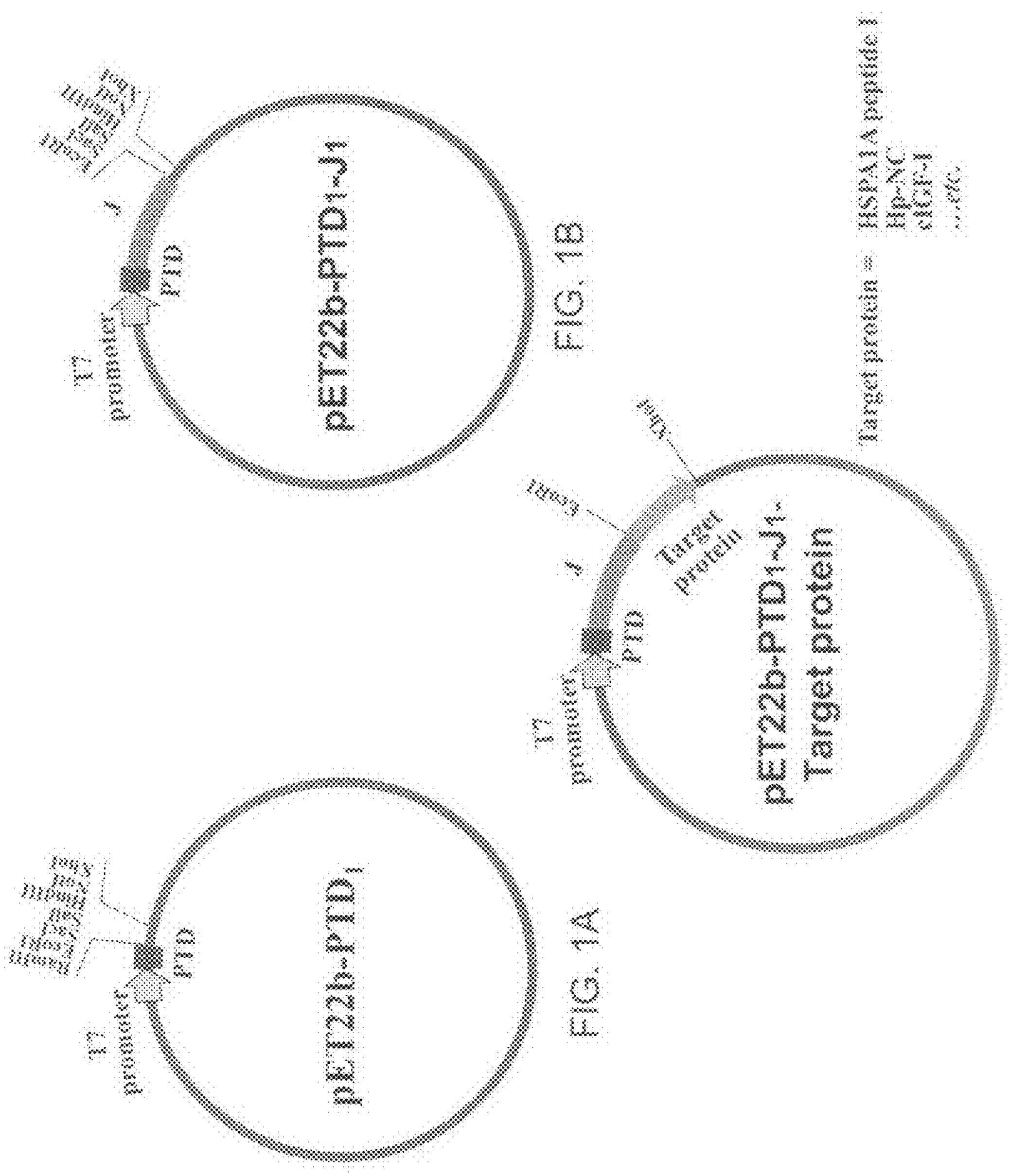
FIGS. 1A-1C illustrate plasmid maps.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "fusion protein," also known as "chimeric protein," refers to "a protein created through the joining of two or more genes which originally coded for separate proteins."

The term "immunogenicity" refers to the ability of antigen to provoke an immune response.

The term "enhancing solubility of a target protein or polypeptide" refers to "a significant increase in the amount of target protein or polypeptide that otherwise form inclusion bodies is expressed in soluble state when compared to a thioredoxin-fused target protein.

The invention is related to a recombinant protein expression vector that can enhance the immunogenicity of a target protein or polypeptide and increase its solubility in a host cell expression system.

An expression vector system containing a Hsp40 family proteins J-domain was designed to examine whether a target protein expressed using the J-domain-containing expression system of the invention would have an increased solubility when compared to the target protein expressed using other expression systems where insoluble inclusion bodies were formed. In addition, a protein transduction domain (PTD) (11 amino acid residues in length) (Ryu et al., 2003; Jones et al., 2005) of HIV Tat protein was fused to the N-terminus of the J-domain to facilitate the recombinant protein $PTD_1J_1$-polypeptide to penetrate cell membranes when the fusion polypeptide would be used as an antigen (Wadia et al., 2004; Kaplan et al., 2005). After penetrating the cell membrane of antigen presenting cells (APCs), the J-domain would target to the Hsp70 ATPase domain and thereby allow the fusion polypeptide to be caught by the Hsp70 substrate binding site. The Hsp70-peptide antigen complex has been known to plays an important role in the process of antigen presentations (Mycko et al., 2004; Bendz et al., 2007).

The invention is related to a recombinant protein expression vector that can enhance the immunogenicity of a target protein or polypeptide, and increase the solubility of a target protein or polypeptide in a host cell expression system. Utilizing the ability of the J-domain of the mammalian Hsp40s in targeting to bacterial DnaK, an *E. coli* expression vector was designed to express recombinant proteins that had been proven forming insoluble inclusion bodies in other expression vectors to investigate whether the J-domain would help folding and thus increased the solubility of the fusion polypeptide/protein. In addition, a protein transduction domain (PTD) (11 amino acid residues in length) (Ryu et al., 2003; Jones et al., 2005) of HIV Tat protein was fused to the N-terminus of the J-domain to facilitate the recombinant protein $PTD_1J_1$-polypeptide to penetrate cell membranes when the fusion polypeptide would be used as an antigen (Wadia et al., 2004; Kaplan et al., 2005). After penetrating the cell membrane of antigen presenting cells (APCs), the J-domain would target to the Hsp70 ATPase domain and thereby allow the fusion polypeptide to be caught by the Hsp70 substrate binding site. The Hsp70-peptide antigen complex has been known to plays an important role in the process of antigen presentations (Mycko et al., 2004; Bendz et al., 2007).

One aspect of the invention relates to a chimeric protein that contains three polypeptide fragments: (a) a first polypeptidyl fragment located at the N-terminal end of the fusion protein that contains a protein transduction domain (PTD) or a fragment thereof having HIV Tat PTD activity; (b) a second polypeptidyl fragment located at the C-terminal end of the first polypeptidyl fragment that contains a J-domain or a fragment thereof having heat shock protein 70 (Hsp70)-interacting activity; and (c) a third polypeptidyl fragment at the C-terminal end of the second polypeptidyl fragment that contains a target protein or a polypeptide. The first polypeptidyl fragment of the chimeric protein may include an amino acid sequence set forth by SEQ ID NO: 1. The second polypeptidyl fragment of the chimeric protein may contain an amino acid sequence set forth by SEQ ID NO: 3.

Another aspect of the invention relates to a chimeric gene that includes three DNA sequences: (a) a first DNA sequence encoding a protein transduction domain (PTD) or a fragment thereof having HIV Tat PTD activity; (b) a second DNA sequence encoding, linked in translation frame with the first DNA sequence, encoding a J-domain or a fragment thereof having heat shock protein 70 (Hsp70)-interacting activity; and (c) a third DNA sequence encoding, linked in translation frame with the second DNA sequence, encoding a target protein or polypeptide.

Another aspect of the invention relates to a chimeric gene that comprises two DNA sequences: (a) a first DNA sequence encoding a protein transduction domain (PTD) or a fragment thereof having HIV Tat PTD activity; and (b) a second DNA sequence encoding, linked in translation frame with the first DNA sequence, encoding a J-domain or a fragment thereof having heat shock protein 70 (Hsp70)-interacting activity.

The J-domain may be at least one selected from the group consisting of a heat shock protein 40 (Hsp40 ) J-domain and a simian virus 40 (SV40) large T antigen (TAg) J-domain. The SV40 TAg J-domain is located within the N-terminal domain (residues 1 to 82) of SV40 TAg. It has been reported that the N-terminal J-domain of TAg shares functional homology with the Hsp40 J domain (DeCaprio et al., 1997). In one embodiment of the invention, the J-domain is a human heat shock protein 40 J-domain.

The first DNA sequence of the chimeric gene may encode a protein transduction domain (PTD) that contains an amino acid sequence set forth by SEQ ID NO: 1. The second DNA sequence of the chimeric gene may encode a J-domain comprising an amino acid sequence set forth by SEQ ID NO: 3.

Another aspect of the invention relates to a method for enhancing immunogenicity and/or solubility of a target protein or polypeptide in a host cell expression system. The method includes the steps of: (a) generating a protein expression vector according to claim 18; (b) transfecting a host cell with the expression vector; (c) culturing the host cell transfected with the expression vector under conditions that permit expression of the target protein or polypeptide; and (d) isolating the target protein or polypeptide.

Further another aspect of the invention relates to a method of expressing a target protein or polypeptide. The method contains the steps of: (a) transfecting a host cell with the expression vector of claim 18; (b) culturing the host cell transfected with the expression vector under conditions that permit expression of the target protein or polypeptide; and (c) isolating the target protein or polypeptide.

Further another aspect of the invention relates to a protein expression vector that comprises one of the aforementioned chimeric genes.

Yet another aspect of the invention relates to an isolated host cell that contains an expression vector having one of the aforementioned chimeric genes.

EXAMPLES

Without intent to limit the scope of the invention, exemplary instruments, apparatus, methods and their related results according to the embodiments of the present invention are given below. Note that titles or subtitles may be used in the examples for convenience of a reader, which should in no way limit the scope of the invention. Theories are proposed and disclosed herein should in no way limit the scope of the invention so long as the invention is practiced according to the invention without regard for any particular theory or scheme of action.

Example 1

Construction of pET22b-$PTD_1$-$J_1$ Expression Vector

FIGS. 1A-1C illustrate three pET22b derivatives plasmids: pET22b-$PTD_1$, pET22b-$PTD_1$-$J_1$, and pET22b-$PTD_1$-target protein (or antigenic protein). These plasmids were generated using the methods as described below.

Plasmid pET22b-$PTD_1$. The plasmid pET22b-$PTD_1$ contains a HIV that $PTD_1$ (native form) gene insert between the restriction enzymes NadI and BamH1, as shown in FIG. 2A. The $PTD_1$ gene, which encodes the amino acid sequence of $PTD_1$ (SEQ ID NO:1), was synthesized using the oligonucleotide pair, $PTD_1$ f (TATGTATGGTCGTAAGAACGTCGTCAGCGTCGTCGTGG; SEQ ID NO: 5) and $PTD_1$ r (GATCCCACGACGACGCTGACGACGTTTCTTACGACCATACA; SEQ ID NO: 6). The oligonucleotide pair encoding the optimized codons of protein transduction domain ($PTD_1$) (SEQ ID NO: 1) for *E. coli* were phosphorylated by polynucleotide kinase before annealing to the double strand form in order to be inserted into the pET22b vector (Novagen, Madison, Wis.) to generate pET22b-$PTD_1$ (FIG. 1A). Before ligating with the $PTD_1$ gene insert, the pET22b vector was co-digested by NdeI and BamHI and dephosphorylated by calf intestine alkaline phosphatase (CIAP). FIG. 2A shows the detailed nucleotide sequence of the plasmid pET22b-$PTD_1$ and encoded $PTD_1$ amino acid sequence.

Plasmid pET22b-$PTD_1$-$J_1$. The plasmid pET22b-$PTD_1$-$J_1$ contains a fusion gene with the $PTD_1$ gene being fused to the N-terminus of the HSP40 J domain gene. The fusion gene encodes a chimeric protein $PTD_1$-$J_1$. The J domain of the HSP40 gene was synthesized by assembly PCR using the oligonucleotides that were designed to obtain optimized codons for *E. coli*. Table 1 lists the nucleotide sequences of the oligonucleotide primers (SEQ ID NOs: 7 to 16) used in the assembly PCR synthesis of the HSP40 J domain. The concentrations of the primers in the assembly PCR reaction mixture were adjusted as follows: 0.5 μM of F1 and R1 and 0.05 μM of F2, F3, R3, and R2, and so on in the reaction mixture. The assembly PCR profile was 2 min at 94° C., 20 sec at 94° C., 40 sec at 40° C., 20 sec at 72° C. of 20 cycles, and 5 min at 72° C.

Figure 3:
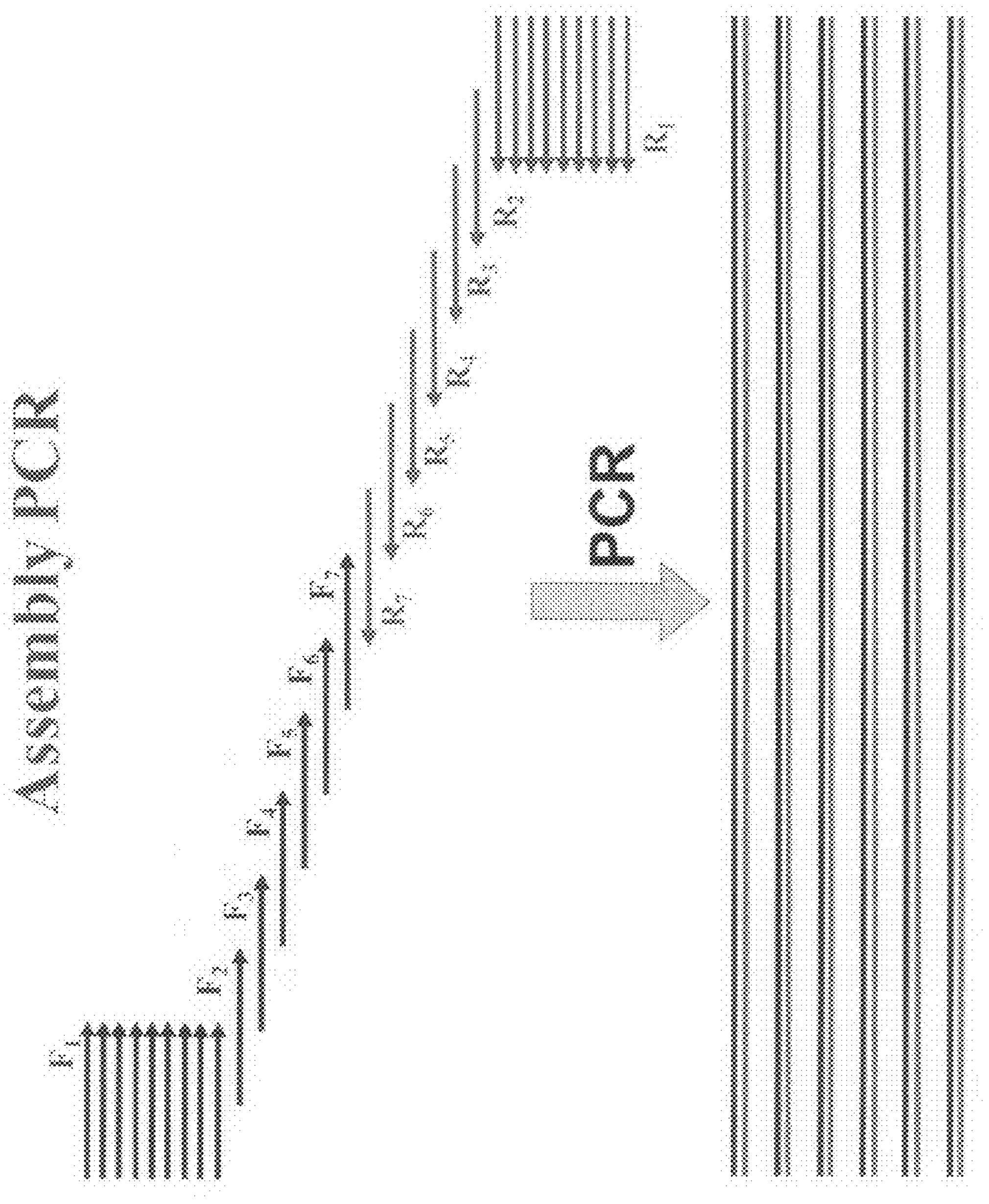
FIG. 3 is a schematic drawing of the assembly PCR.

The PCR product was cloned into pGEM-T Easy vector (Promega) for colony selection and DNA sequencing. The plasmid with correct DNA sequence encoding Hsp40-J domain (SEQ ID NO: 3) was co-digested by BamHI and EcoRI to remove the 0.2 kb inserted DNA fragment from pGEM-T Easy vector. This DNA fragment was then inserted into pET22b-$PTD_1$ vector, which had been digested by BamHI/EcoRI and CIAP, to generate the pET22b-$PTD_1$-$J_1$ expression vector (FIG. 1B). FIG. 2B shows the detailed nucleotide sequence of the plasmid pET22b-$PTD_1$-$J_1$ and the amino acid sequence of the encoded fusion protein $PTD_1$-$J_1$. FIG. 3 is a schematic drawing of the assembly PCR, which is an artificial synthesis of long DNA sequences by performing PCR on a pool of long oligonucleotides with short overlapping segments.

TABLE 1

| Primer | Sequence | Sequence ID |
|---|---|---|
| J1 nBF1 | tggatcctgggtaaagattactaccagactcacggtctc | SEQ ID NO: 7 |
| F2 | tactaccagactcacggtctcgctcgtggtgcatctgatgatgaaatc | SEQ ID NO: 8 |
| F3 | ggtgcatctgatgatgaaatcaaacgtgcttaccgtcgtcaggcactg | SEQ ID NO: 9 |
| F4 | gcttaccgtcgtcaggcactgcgttaccatccagacaaaaacaaagaa | SEQ ID NO: 10 |
| F5 | taccatccagacaaaaacaaagaaccgggtgcagaagagaaattc | SEQ ID NO: 11 |
| F6 | ccgggtgcagaagagaaattcaaagagatcgcagaagcatacgacgtt | SEQ ID NO: 12 |
| EcoRI R1 | cgaaattcgcaccaccagaaccacctttcagaccttc | SEQ ID NO: 13 |
| R2 | agaaccacctttcagaccttcttcaccgtaacggtcgaagatttcacg | SEQ ID NO: 14 |
| R3 | gtaacggtcgaagatttcacgtttacgtggatcgctcagaacgtcgta | SEQ ID NO: 15 |
| R4 | tggatcgctcagaacgtcgtatgcttctgcgatctc | SEQ ID NO: 16 |

Plasmid pET22b-$PTD_1$-$J_1$-Target protein. The plasmid pET22b-$PTD_1$-$J_1$-target protein contains a fusion gene encoding a chimeric protein, $PTD_1$-$J_1$-target protein. Target proteins that were inserted into the expression vector pET22b-$PTD_1$-$J_1$ included those proteins that had been proven to form insoluble inclusion bodies due to the solubility issue when using other expression vectors, and small peptides that are weak in inducing immunogenicity and/or having solubility issues in *E. coli* expression system. A DNA fragment comprising a codon-optimized cDNA sequence encoding a target protein to be expressed in the pET22b-$PTD_1$-$J_1$ expression vector was synthesized by PCR, and the PCR product was then inserted into the pET22b-$PTD_1$-$J_1$ vector at EcoRI and XhoI sites to generate the plasmid pET22b-$PTD_1$-

$J_1$-target protein. The resulting plasmid was transformed into *E. coli* Rosetta (Novagen) competent cells to obtain clones.

Example 2

Expression and Analyses of Recombinant Proteins

Chimeric proteins, $PTD_1$-$J_1$-target protein, were expressed in *E. coli* cultures containing corresponding expression plasmids. In brief, the colony resistant to ampicillin and chloramphenicol was cultured and amplified in TYD medium (10 g trypton, 20 g yeast extract, 5 g NaCl, 2 g Dextrose per liter, pH 7.2). Once $OD_{600}$ reached 0.3±0.1, the bacterial culture was induced with isopropylthio-β-D-galactoside (IPTG; Promega, USA) at a final concentration of 1 mM at 37° C. in a rotating incubator shaken at 225 rpm. After the IPTG induction, the cells were collected by centrifugation at 5,000×g for 10 min, washed once with PBS, resuspended in PBS and homogenized by sonication. The sonicated lysates were centrifuged at 15,000×g for 30 min. Twenty microliters of total lysates from 0.3 $OD_{600}$ unit of *E. coli* cells were mixed with 30 μL of 2×SDS-PAGE loading buffer, and the mixture was loaded into each well of the gel. The protein bands were visualized by Coomassie brilliant blue R250 staining of the gel, and scanned by laser densitometer (Personal Densitometer SI, Molecular Dynamics). The amount of each recombinant protein over the amount of total protein was calculated and represented as percentage weight.

Example 3

Expression of Human HSPA1A Peptide I

A DNA fragment comprising a codon-optimized cDNA sequence (SEQ ID NO: 17) encoding the amino acid sequence (SEQ ID NO: 18) of human heat shock 70 kDa protein 1A (HSPA1A) Peptide I was synthesized by assembly PCR using the primers listed in Table 2. The assembly PCR profile was 2 min at 94° C., 20 sec at 94° C., 40 sec at 40° C., 20 sec at 72° C. of 20 cycles, and 5 min at 72° C. The PCR product was then inserted in the expression vector pET22b-$PTD_1$-$J_1$ to generate the plasmid pET22b-$PTD_1$-$J_1$-HSPA1A peptide I using the method described in Example 1.

Plasmid pET22b-$PTD_1$-$J_1$-HSPA1A peptide I that carried the genes encoding the recombinant protein $PTD_1$-$J_1$-HSPA1A peptide I was transformed into *E. coli* Rosetta. The recombinant protein expression was induced by IPTG according to the method described above for up to 16 hours and the amounts of protein induced in the cell extract determined as in Example 2.

Figures 4A, 4B:
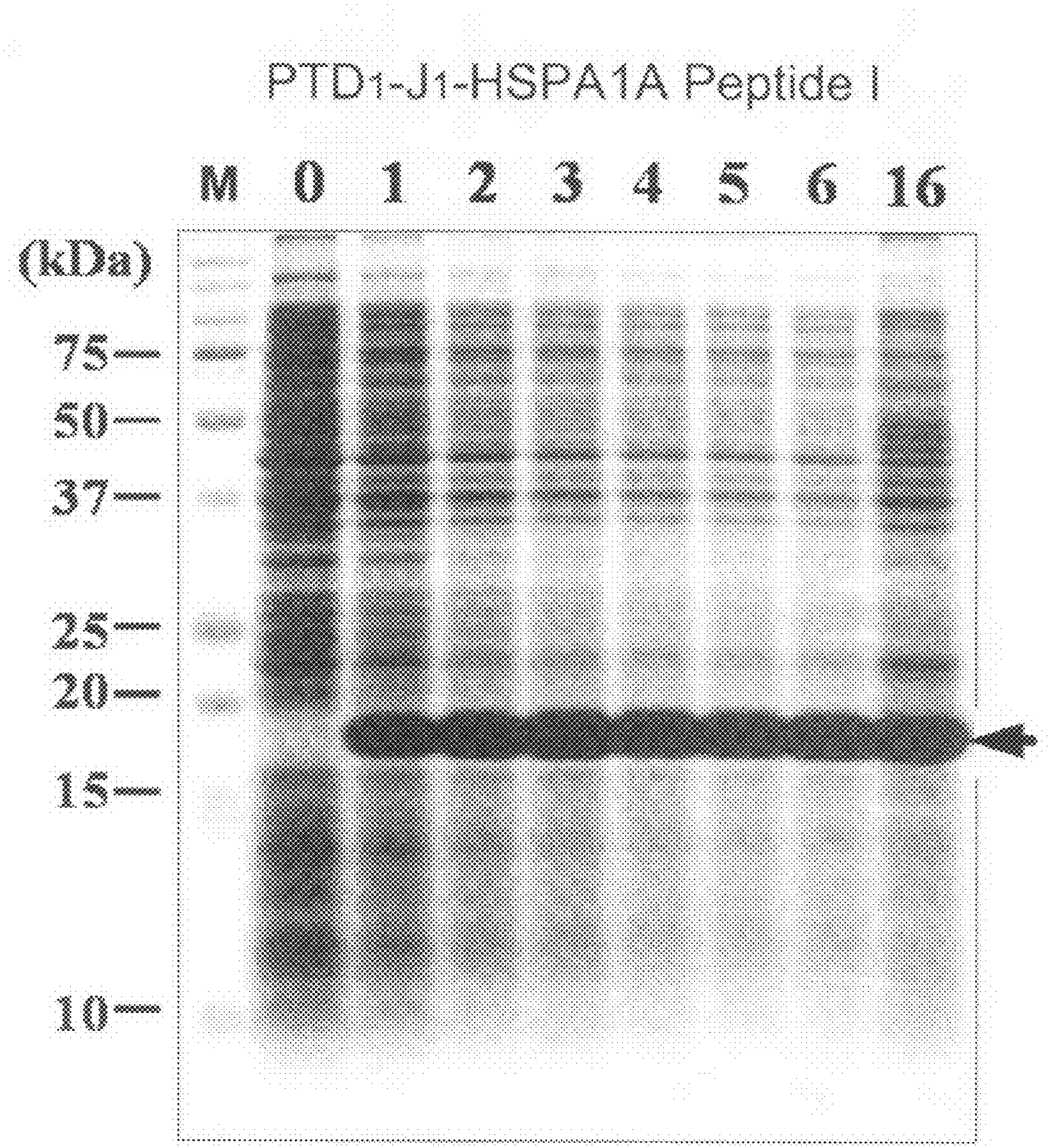
FIG. 4A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-HSPA1A peptide I.
FIG. 4B is a chart showing the weight percentage of the recombinant protein relative to the total proteins after the various induction periods.

FIG. 4A shows a Coomassie® blue stained SDS-PAGE gel analysis of *E. coli* whole cell lysates. The protein bands shown between 15 kDa and 20 kDa (indicated by an arrow) correspond to the target protein, pET22b-$PTD_1$-$J_1$-HSPA1A peptide I. Lane 1: standard molecular weight marker. Lanes 2-9: whole cell lysates after the IPTG induction, where "0 hr" stands for "uninduced."

The effect of induction period of IPTG induction on the yield of the $PTD_1$-$J_1$-HSPA1A peptide I expression was quantitated and represented by the weight percentage of the recombinant $PTD_1$-$J_1$-HSPA1A peptide I over the total proteins. As shown in FIG. 4B, the induction reached a plateau after about 4 hrs. The expression of $PTD_1$-$J_1$-HSPA1A peptide I declined as the IPTG induction was extended to 16 hours.

Example 4

Expression of Human HSPA1A Peptide II

A DNA fragment comprising a codon-optimized cDNA sequence (SEQ ID NO: 25) encoding the amino acid sequence (SEQ ID NO: 26) of human heat shock 70 kDa protein 1A (HSPA1A) peptide II was synthesized by assembly PCR using the primers (SEQ ID NO: 27 to SEQ ID NO: 33) listed in Table 3. The assembly PCR profile was 2 min at 94° C., 20 sec at 94° C., 40 sec at 40° C., 20 sec at 72° C. of 20 cycles, and 5 min at 72° C. The PCR product was then inserted in the expression vector pET22b-$PTD_1$-$J_1$ to generate the plasmid pET22b-$PTD_1$-$J_1$-HSPA1A peptide II using the method described in Example 1.

TABLE 2

| Primer | Sequence | Sequence ID |
|---|---|---|
| RI-I-f1 | gaattctagcagcagcacccaggcgagcctggaaattgatagcctgttt | SEQ ID NO: 19 |
| I-f2 | agcctggaaattgatagcctgtttgaaggcattgat ttttataccagc | SEQ ID NO: 20 |
| I-f3 | gtttgaaggcattgatttttataccagcatt acccgtgcgcgttttgaa | SEQ ID NO: 21 |
| I-r3 | gggtgctacgaaacagatcgctgcacagttcttcaaaacgcgcacgggt | SEQ ID NO: 22 |
| I-r2 | catcacgcagcgctttttccaccggttccagggtgctacgaaacagatc | SEQ ID NO: 23 |
| Xho-I-r1 | ctcgagaatctgcgctttatccagtttcgcatc acgcagcgctttttc | SEQ ID NO: 24 |

TABLE 3

| Primer | Sequence | Sequence ID |
|---|---|---|
| RI-II-f1 | gaattctaacgtaaccgctactgacaaatccactggtaaagctaacaag | SEQ ID NO: 27 |
| II-f2 | tccactggtaaagctaacaagatcaccatcaccaacgacaaaggtcgtc | SEQ ID NO: 28 |
| II-f3 | atcaccaacgacaaaggtcgtctgtccaaggaagagatcgagcgtatgg | SEQ ID NO: 29 |
| II-f4 | aaggaagagatcgagcgtatggttcaggaagctgaaaagtacaag | SEQ ID NO: 30 |
| II-r3 | acgctgaacttcgtcttcagccttgtacttttcagcttcctgaacc | SEQ ID NO: 31 |
| II-r2 | agcgttcttagcggaaacacgttcacgctgaacttcgtcttcagc | SEQ ID NO: 32 |
| Xho-II-r1 | ctcgaggaaagcgtaggattccagagcgttcttagcggaaacacgttca | SEQ ID NO: 33 |

Plasmid pET22b-$PTD_1$-$J_1$-HSPA1A peptide II that carried the genes encoding the recombinant protein $PTD_1$-$J_1$-HSPA1A peptide II was transformed into *E. coli* Rosetta. The recombinant protein expression was induced by IPTG according to the method described above. The amount of protein induced in the cell lysate over the 16 hours IPTG induction was monitored as in Example 2 above.

Figures 5A, 5B:
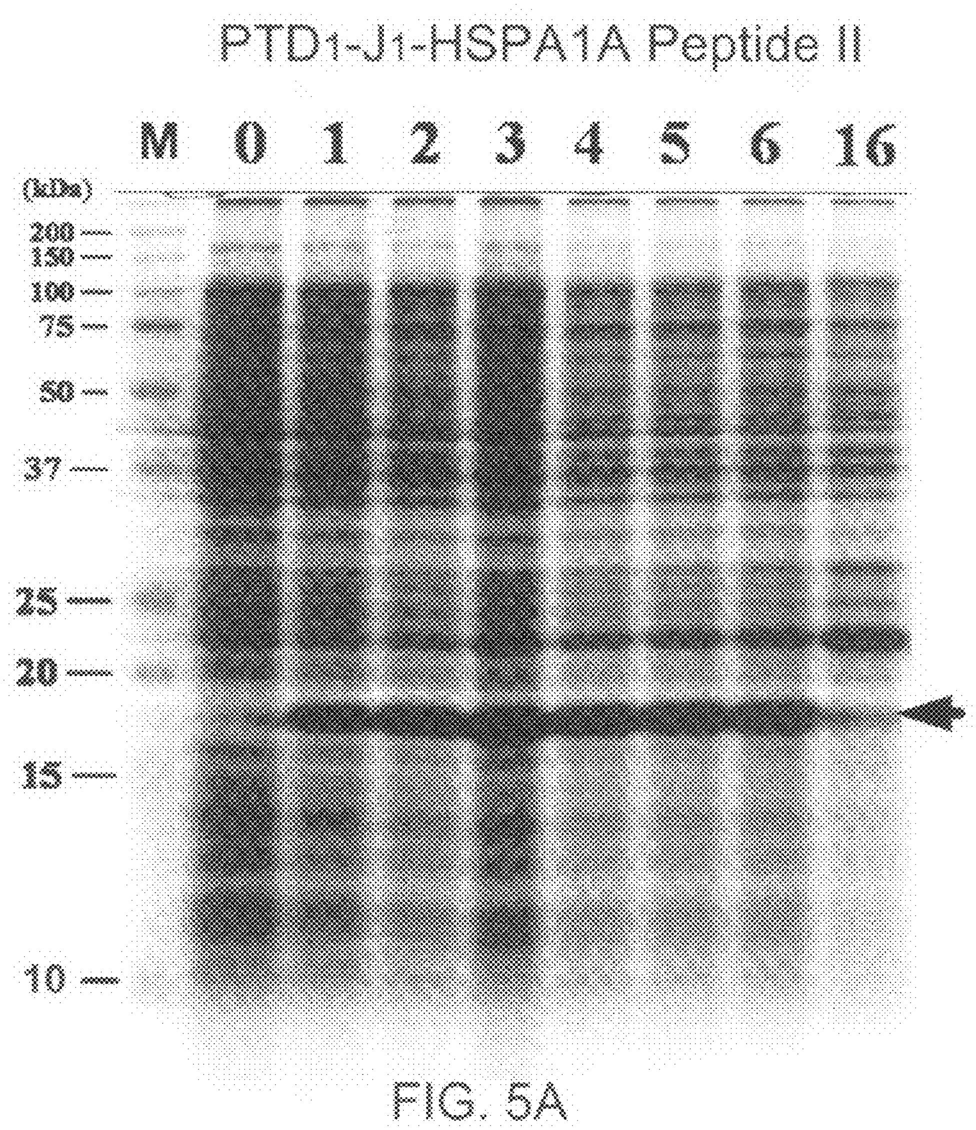
FIG. 5A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-HSPA1A peptide II.
FIG. 5B is a chart showing the weight percentage of the recombinant protein relative to the total proteins after the various induction periods.

FIG. 5A shows a Coomassie® blue stained SDS-PAGE gel analysis of *E. coli* whole cell lysates. The protein bands shown between 15 kDa and 20 kDa (indicated by an arrow) correspond to the chimera protein P $PTD_1$-$J_1$-HSPA1A peptide II. Lane 1: standard molecular weight marker. Lanes 2-9: whole cell lysates after the IPTG induction, where "0 hr" stands for "uninduced."

The amount of the $PTD_1$-$J_1$-HSPA1A peptide II expression after each induction period was quantitated and the yield expressed as the weight percentage of the recombinant $PTD_1$-$J_1$-HSPA1A peptide II over the total proteins. As shown in FIG. 5B, the induction reached a plateau after 4 hrs. The expression of $PTD_1$-$J_1$-HSPA1A peptide II declined as the IPTG induction was extended to 16 hours.

Example 5

Expression of Human HSPA1A Peptide III

A DNA fragment comprising a codon-optimized cDNA sequence (SEQ ID NO: 34) encoding the amino acid sequence (SEQ ID NO: 35) of human heat shock 70 kDa protein 1A (HSPA1A) peptide III was synthesized by assembly PCR using the primers (SEQ ID NO: 36 to SEQ ID NO: 42) listed in Table 4. The assembly PCR profile was 2 min at 94° C., 20 sec at 94° C., 40 sec at 40° C., 20 sec at 72° C. of 20 cycles, and 5 min at 72° C. The PCR product was then inserted in the expression vector pET22b-$PTD_1$-$J_1$ to generate the plasmid pET22b-$PTD_1$-$J_1$-HSPA1A peptide III using the method described in Example 1.

TABLE 4

| Primer | Sequence | Sequence ID |
|---|---|---|
| RI-III-f1 | gaattctgaagatgaaggcctgaaaggcaaaattagcgaagcggat | SEQ ID NO: 36 |
| III-f2 | ggcaaaattagcgaagcggataagaaaaaggtgctg gataaatgccag | SEQ ID NO: 37 |
| III-f3 | ggtgctggataaatgccag gaagtgattagctggctg gatgcgaacacc | SEQ ID NO: 38 |
| III-f4 | gctggatgcgaacaccctggcggaaaaagatgaattt gaacataaacgt | SEQ ID NO: 39 |
| III-r3 | ttccagttctttacgtttatgttcaaattcatctttttccgccag | SEQ ID NO: 40 |
| III-r2 | cgggttgcacacctgttccagttctttacgtttatgttcaaattcatc | SEQ ID NO: 41 |
| Xho-III-r1 | ctggagcgcgccctgatacaggccgctaataatcgggttgcacacctg | SEQ ID NO: 42 |

Plasmid pET22b-$PTD_1$-$J_1$-HSPA1A peptide III that carried the genes encoding the recombinant protein $PTD_1$-$J_1$-HSPA1A peptide III was transformed into *E. coli* Rosetta. The recombinant protein expression was induced by IPTG according to the method described above. The amount of protein induced in the cell lysate was monitored over the 16 hours IPTG induction as in Example 2 above.

Figures 6A, 6B:
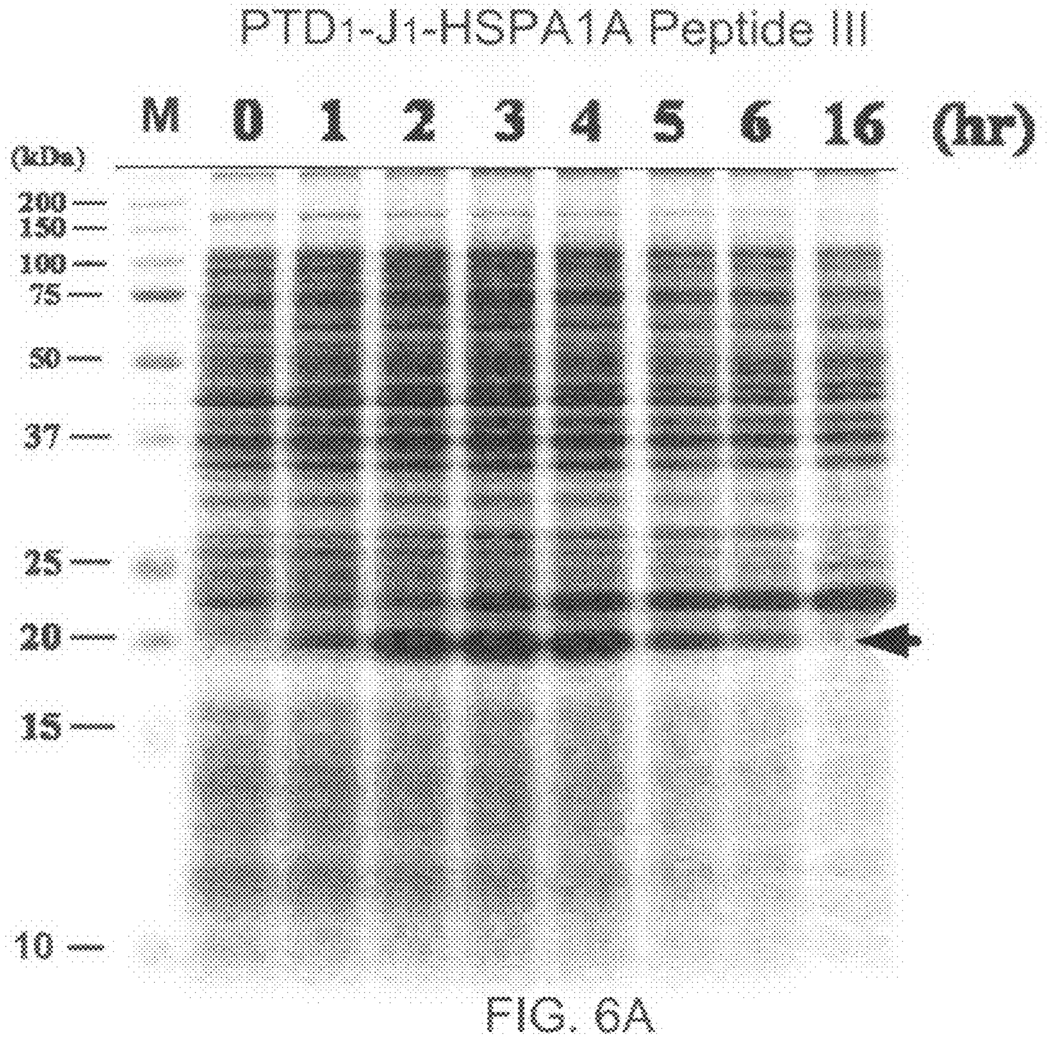
FIG. 6A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-HSPA1A peptide III.
FIG. 6B is a chart showing the weight percentage of the recombinant protein relative to the total proteins after the various induction periods.

FIG. 6A shows a Coomassie® blue stained SDS-PAGE gel analysis of *E. coli* whole cell lysates. The protein bands shown between 15 kDa and 20 kDa (indicated by an arrow) correspond to the chimera protein $PTD_1$-$J_1$-HSPA1A peptide III. Lane 1: standard molecular weight marker. Lanes 2-9: whole cell lysates after the IPTG induction, where "0 hr" stands for "uninduced."

The amount of the $PTD_1$-$J_1$-HSPA1A peptide III expression after each induction period was quantitated and the yield represented by the weight percentage of the recombinant $PTD_1$-$J_1$-HSPA1A peptide III over the total proteins. As shown in FIG. 6B, the induction reached a plateau after 2 hrs. The expression of $PTD_1$-$J_1$-HSPA1A peptide III declined as the IPTG induction was extended.

Example 6

Expression of Chicken IGF-I

A DNA fragment comprising a codon-optimized cDNA sequence (SEQ ID NO: 43) encoding the amino acid sequence (SEQ ID NO: 44) of chicken IGF-I peptide (cIGF-I)

was synthesized by assembly PCR using the primers (SEQ ID NO: 45 to SEQ ID NO: 51) listed in Table 5. The assembly PCR profile was 2 min at 94° C., 20 sec at 94° C., 40 sec at 40° C., 20 sec at 72° C. of 20 cycles, and 5 min at 72° C. The PCR product was then inserted in the expression vector pET22b-$PTD_1$-$J_1$ to generate the plasmid pET22b -$PTD_1$-$J_1$-cIGF-I using the method described in Example 1.

TABLE 5

| Primer | Sequence | Sequence ID |
|---|---|---|
| RI-F1 new | gaattctggtccagaaaccctgtgtggtgcagaactggttgatgcactgca gttcgtg | SEQ ID NO: 45 |
| F2 | gaactggttgatgcactgcagttcgtgtgtggtgatcgtggtttctac | SEQ ID NO: 46 |
| F3 | ggtgatcgtggtttctacttcagcaaaccgactggttatggtagctctagc | SEQ ID NO: 47 |
| F4 | ggttatggtagctctagccgtcgtctgcatcacaaaggtattgtggatg | SEQ ID NO: 48 |
| F5 | cacaaaggtattgtggatgaatgttgctttcagagctgtgatctgcgtcg | SEQ ID NO: 49 |
| R2 | gattggtgcacagtacatttccagacgacgcagatcacagctctg | SEQ ID NO: 50 |
| Xho-R1 | ctcgagtgcgcttttcggtggtttgattggtgcacagtacatttcc | SEQ ID NO: 51 |

Plasmid pET22b-$PTD_1$-$J_1$-cIGF-I that carried the genes encoding the recombinant protein $PTD_1$-$J_1$-cIGF-I was transformed into *E. coli* Rosetta. The recombinant protein expression was induced by IPTG according to the method described above for up to 6 hours and the amounts of proteins induced in the cell extracts determined as in Example 2 above.

Figures 7A, 7B:
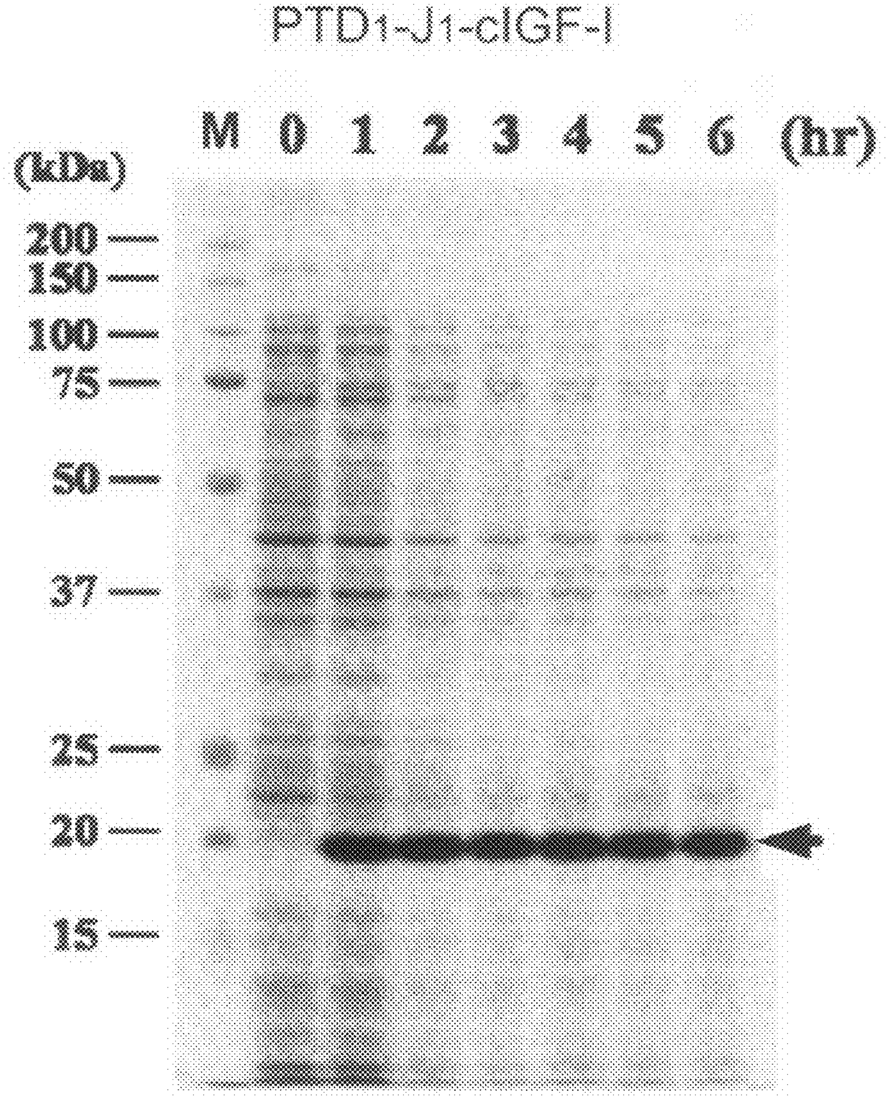
FIG. 7A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-cIGF-I.
FIG. 7B is a chart showing the weight percentage of the recombinant protein relative to the total proteins after the various induction periods.

FIG. 7A shows a Coomassie® blue stained SDS-PAGE gel analysis of *E. coli* whole cell lysates. The protein bands shown around 20 kDa (indicated by an arrow) correspond to the chimera protein $PTD_1$-$J_1$-cIGF-I. Lane 1: standard molecular weight marker (M). Lanes 2-8: whole cell lysates after the IPTG induction, where "0 hr" stands for "uninduced." The amount of the $PTD_1$-$J_1$-cIGF-I expression after each induction period was quantitated and the yield represented by the weight percentage of the recombinant protein $PTD_1$-$J_1$-cIGF-I over the total proteins. As shown in FIG. 7B, the induction reached a plateau after about 2 to 4 hrs.

Example 7

Expression of Avian Influenza Virus HA (H5) Receptor Binding Domain (RBD)

A DNA fragment, which comprises a native viral cDNA sequence (SEQ ID NO: 52) encoding the amino acid sequence (SEQ ID NO: 53) of the receptor binding domain (RBD) of avian Influenza virus Hemagglutin (HA) subtype H5, was synthesized by PCR using the primer pair (SEQ ID NOs: 54 and 55) listed in Table 6, and avian influenza virus hemagglutinin (HA) subtype H5 cDNA as a DNA template (GeneBank accessing number: EF419243). The PCR profile was 2 min at 94° C., 20 sec at 94° C., 40 sec at 60° C., 20 sec at 72° C. of 20 cycles, and 5 min at 72° C. The PCR product was inserted in the expression vector pET22b-$PTD_1$-$J_1$ to generate the plasmid pET22b-$PTD_1$-$J_1$-HA_RBD using the method described in Example 1 above.

TABLE 6

| Primer | Sequence | Sequence ID |
|---|---|---|
| RI HA-RBD f | tgaattcgaaacacctattgagcagaataaac | SEQ ID NO: 54 |
| Xho HA-RBD r | tctcgagaattgttgagtcccctttcttgac | SEQ ID NO: 55 |

Plasmid pET22b-$PTD_1$-$J_1$-HA_RBD that carried the genes encoding the recombinant protein $PTD_1$-$J_1$-HA_RBD was transformed into *E. coli* Rosetta. The recombinant protein expression was induced by IPTG according to the method described above. The amount of protein induced in the cell lysate was monitored over the 16 hours IPTG induction as in Example 2 above.

Figures 8A, 8B:
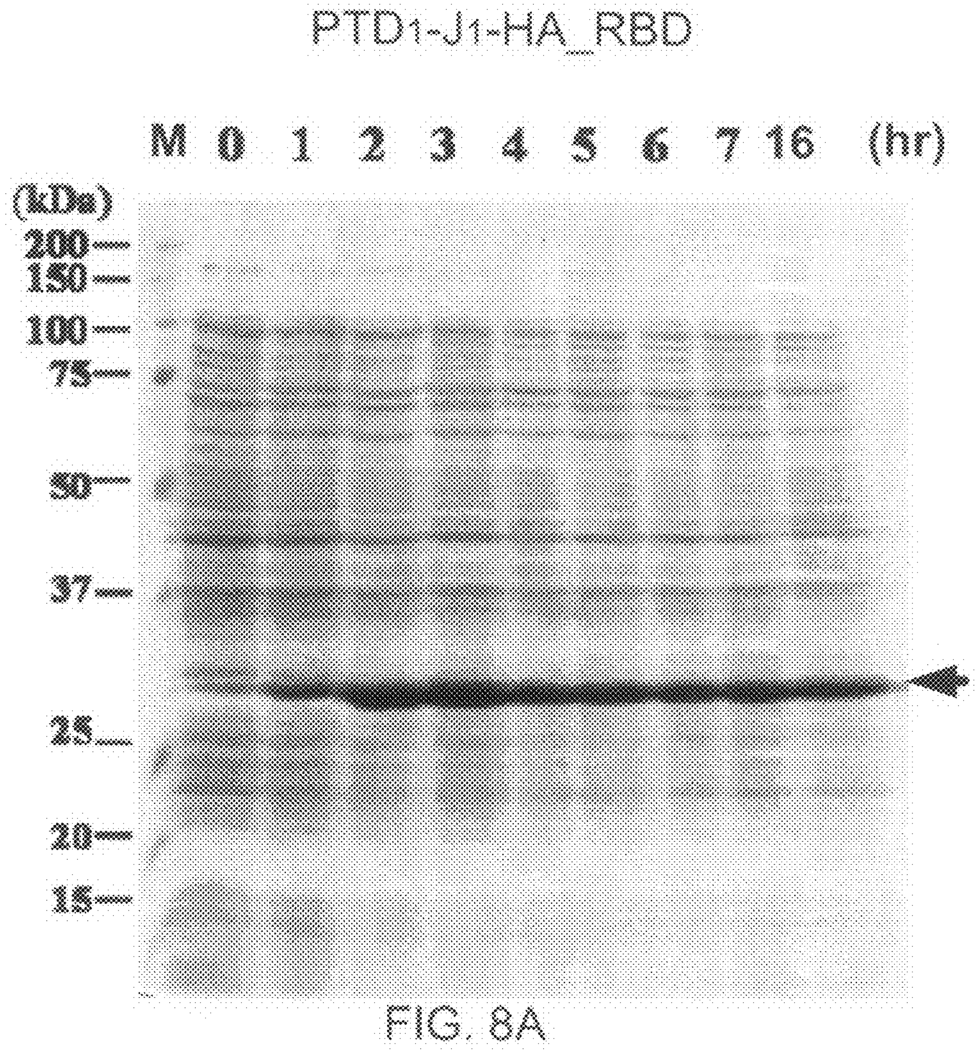
FIG. 8A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-HA_RBD.
FIG. 8B is a chart showing the weight percentage of the recombinant protein relative to the total proteins after the various induction periods.

FIG. 8A shows a Coomassie® blue stained SDS-PAGE gel analysis of *E. coli* whole cell lysates. The protein bands shown between around 37 kDa and 25 kDa (indicated by an arrow) correspond to the chimera protein $PTD_1$-$J_1$-HA_RBD. Lane 1: standard molecular weight marker (M). Lanes 2-10: whole cell lysates after the IPTG induction, where "0 hr" stands for "uninduced." The amount of the $PTD_1$-$J_1$-HA_RBD expression after each induction period was quantitated and the yield represented by the weight percentage of the recombinant protein $PTD_1$-$J_1$-HA_RBD over the total proteins. As shown in FIG. 8B, the induction reached a plateau after about 3 hrs.

Example 8

Expression of Hepatitis C Virus Core Protein

A DNA fragment, which comprises a native viral cDNA sequence (SEQ ID NO: 56) encoding the amino acid sequence (SEQ ID NO: 57) of the hepatitis C virus (HCV) core protein, was synthesized by PCR using the primer pair (SEQ ID NOs: 58 and 59) listed in Table 7 and a HCV cDNA that was reversely transcribed from a serum sample of an acute, hepatitis C infected-patent as a DNA template. The PCR profile was 2 min at 94° C., 20 sec at 94° C., 40 sec at 60° C., 20 sec at 72° C. of 40 cycles, and 5 min at 72° C. The PCR product was inserted in the expression vector pET22b-$PTD_1$-$J_1$ to generate the plasmid pET22b-$PTD_1$-$J_1$-HCV-core protein using the method described in Example 1 above.

TABLE 7

| Primer | Sequence | Sequence ID |
|---|---|---|
| RI-Core f | tgaattcgatgagcacaaatcctaaacctc | SEQ ID NO: 58 |
| Xho-Core r | tctcgagagcagagaccggaacggtgat | SEQ ID NO: 59 |

Plasmid pET22b-$PTD_1$-$J_1$-HCV-core protein that carried the genes encoding the recombinant protein $PTD_1$-$J_1$-HCV-core protein was transformed into *E. coli* Rosetta. The recombinant protein expression was induced by IPTG according to the method described above. The amount of protein induced in the cell lysate was monitored over the 16 hours IPTG induction as in Example 2 above.

Figures 9A, 9B:
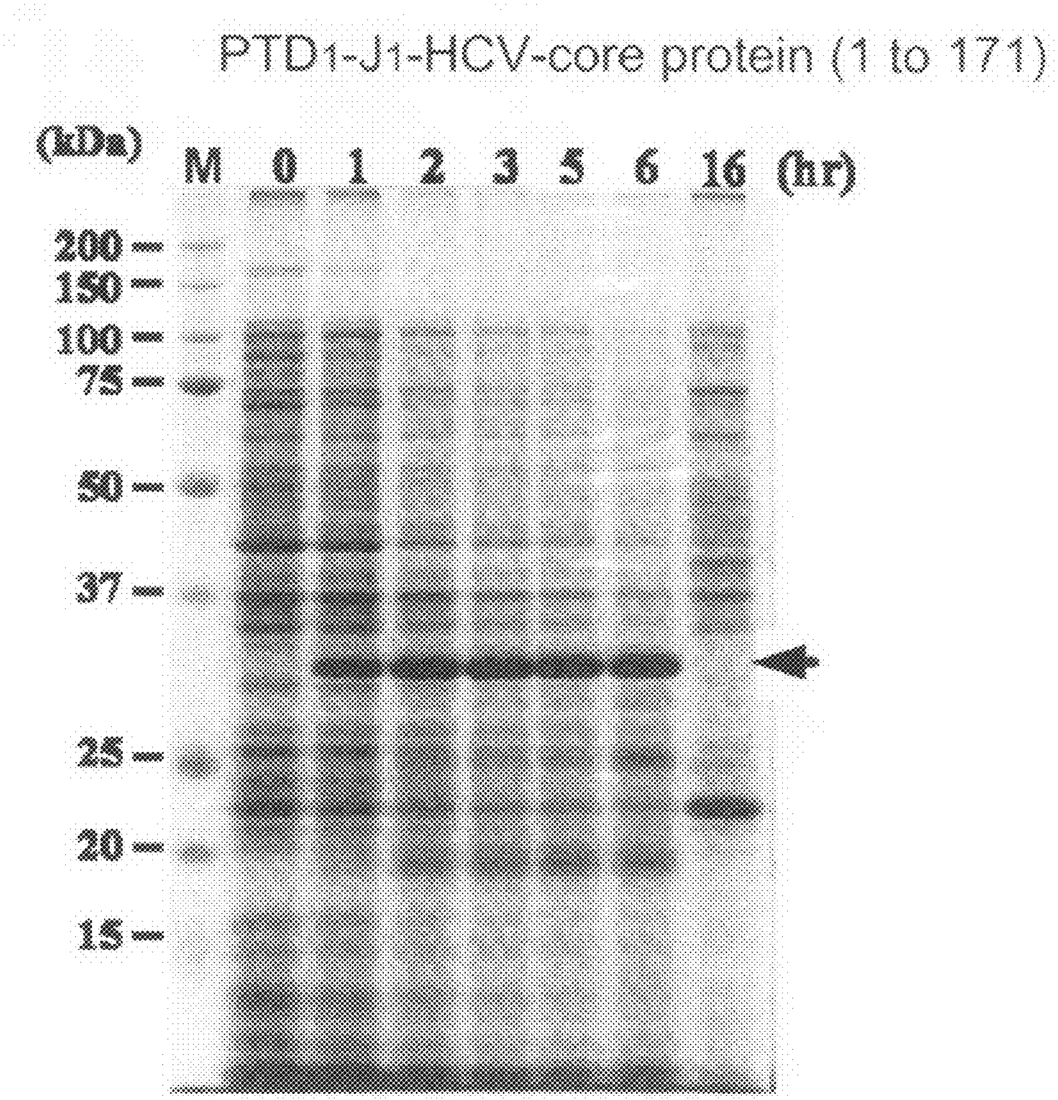
FIG. 9A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-HCV-core protein.
FIG. 9B is a chart showing the weight percentage of the recombinant protein relative to the total proteins after the various induction periods.

FIG. 9A shows a Coomassie® blue stained SDS-PAGE gel analysis of *E. coli.* whole cell lysates. The protein bands shown between around 37 kDa and 25 kDa (indicated by an arrow) correspond to the chimera protein $PTD_1$-$J_1$-HCV-core protein. Lane 1: standard molecular weight marker (M). Lanes 2-8: whole cell lysates after the IPTG induction, where “0 hr” stands for “uninduced.” The amount of the $PTD_1$-$J_1$-HCV core protein expression after each induction period was quantitated and the yield represented by the weight percentage of the recombinant protein $PTD_1$-$J_1$-HCV core protein over the total proteins. As shown in FIG. 9B, the induction reached a plateau after about 5 to 6 hrs.

Example 9

Expression of Human Haptoglobin Fusion Polypeptide

A fusion gene comprising a nucleotide sequence (SEQ ID NO: 60) that encoded an amino acid sequence (SEQ ID NO: 61) of haptoglobin α-chain fusion polypeptide, HpNC, was synthesized by assembly PCR using the primers (SEQ ID NO: 62 to SEQ ID NO: 65) listed in Table 8. The fusion polypeptide HpNC comprises a peptide fragment from the N-terminal portion (DSGNDVTDIADDG, the amino acid residues 1 to 13 of SEQ ID NO: 61) of the mature haptoglobin, a linker (-GSGG-), and a peptide fragment from the C-terminal portion (RHYEGSTVPEKKTPKS, the amino acid residues 18 to 33 of SEQ ID NO: 61) of the premature haptoglobin α-chain. The assembly PCR profile was 2 min at 94° C., 20 sec at 94° C., 40 sec at 40° C., 20 sec at 72° C. of 20 cycles, and 5 min at 72° C. The PCR product was inserted in the expression vector pET22b-$PTD_1$-$J_1$ to generate the plasmid pET22b-$PTD_1$-$J_1$-HpNC using the method described in Example 1.

Plasmid pET22b-$PTD_1$-$J_1$-HpNC that carried the genes encoding the recombinant protein $PTD_1$-$J_1$-HpNC was transformed into *E. coli* Rosetta. The recombinant protein expression was induced by IPTG according to the method described above for up to 6 hours, and the amounts of proteins in cell extracts determined as in Example 2.

TABLE 8

| Primer | Sequence | Sequence ID |
|---|---|---|
| RI-F1 | agaattctgatagcggcaacgatgtgaccgatattgcggatgatggtgg | SEQ ID NO: 62 |
| F2 | tgaccgatattgcggatgatggtggtagtggtggtcgtcattat | SEQ ID NO: 63 |
| F3 | atggtggtagtggtggtcgtcattatgaaggtagcaccgtt | SEQ ID NO: 64 |
| R2 | ggttttcttctccggaacggtgctaccttcataatgacgaccaccac | SEQ ID NO: 65 |
| Xho-R1 | tctcgagaccaccgctctttggggttttcttctccggaacggtgcta | SEQ ID NO: 66 |

Figures 10A, 10B:
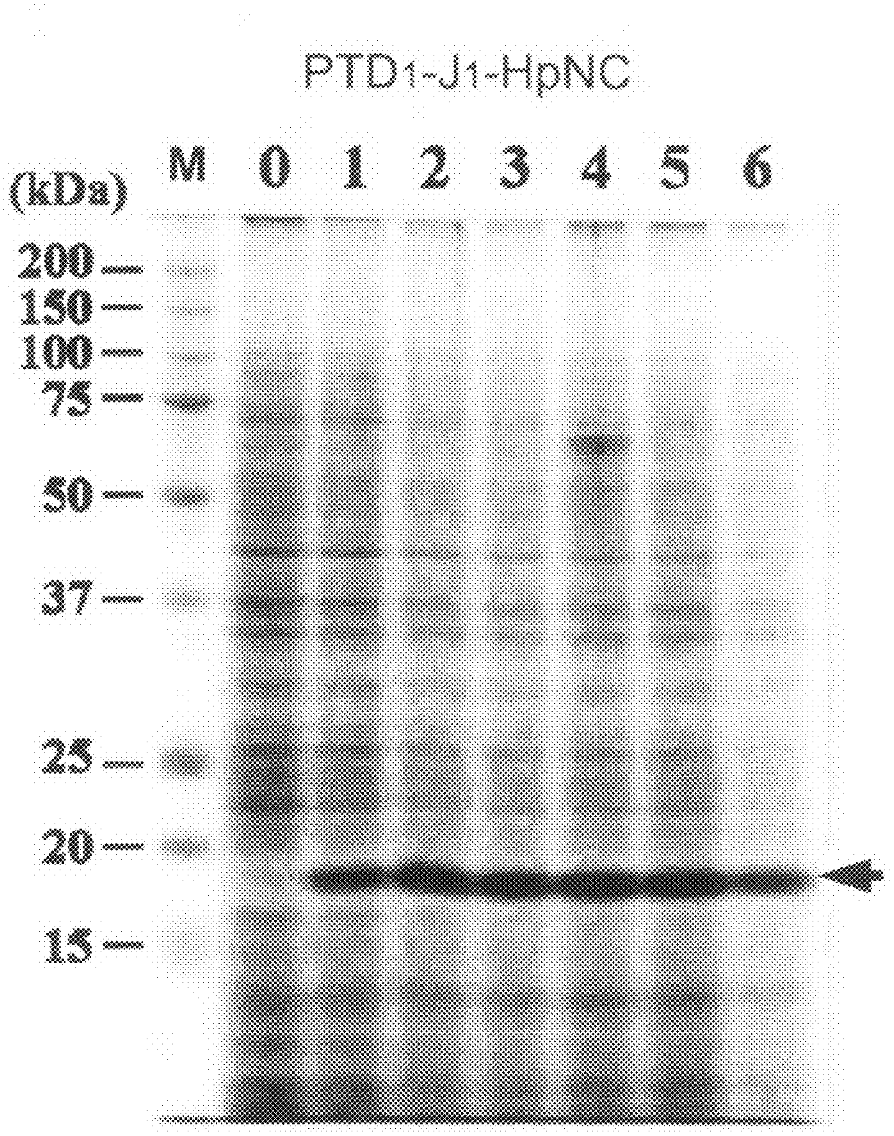
FIG. 10A is a photograph of SDS-PAGE gel electrophoresis of the protein samples from *E. coli* whole cell lysates. M stands for protein molecular weight marker; lanes 2-9: protein bands from the whole cell lysates after the indicated induction period; "0" stands for "un-induced." The arrow indicates the protein band of the target recombinant protein, $PTD_1$-$J_1$-HpNC.
FIG. 10B is a chart showing the weight percentage of the recombinant protein relative to the total proteins after the various induction periods.

FIG. 10A shows a Coomassie® blue stained SDS-PAGE gel analysis of *E. coli* whole cell lysates. The protein bands shown between around 15 kDa and 20 kDa (indicated by an arrow) correspond to the fusion polypeptide $PTD_1$-$J_1$-HpNC. Lane 1: standard molecular weight marker (M). Lanes 2-10: total whole cell lysates after the IPTG induction, where “0 hr” stands for “uninduced.” The amount of the $PTD_1$-$J_1$-HpNC expression after each induction period was quantitated and the yield expressed as the weight percentage of the recombinant protein $PTD_1$-$J_1$-HpNC over the total proteins. As shown in FIG. 10B, the induction reached a plateau after about 3 hrs.

Example 10

Expression of Neutrophile Peptide-1

A cDNA clone comprising a nucleotide sequence (SEQ ID NO: 67) that encodes an amino acid sequence (SEQ ID NO: 68) of Neutrophile peptide-1 (NP-1) was obtained by screening a rabbit intestine cDNA library. The cDNA fragment was inserted into the expression vector pET22b-$PTD_1$-$J_1$ to generate the plasmid pET22b-$PTD_1$-$J_1$-NP-1. Plasmid pET22b-$PTD_1$-$J_1$-NP-1 that carried the genes encoding the recombinant protein $PTD_1$-$J_1$-NP-1 was transformed into *E. coli*

Rosetta. The recombinant protein expression was induced by IPTG according to the method described above.

Example 11

Target Protein-Specific Immunogenicity

Immunization of animals. Balb/c Mice of 5-week-old were immunized subcutaneously with 50 μg of the recombinant protein $PTD_1$-$J_1$-NP-1 emulsified in TiterMAX Gold adjuvant. Boosts were carried out every 2 weeks. Five days after the second boost, the sera of the mice were collected and assayed for the antibody against the recombinant protein $PTD_1$-$J_1$-NP-1. The specificity of anit-serum against NP-1 was determined using the dot blotting assay.

Dot Blotting Assay. Solutions containing various amounts of recombinant proteins (antigens), $PTD_1$-$J_1$-NP-1, $PTD_1$-$J_1$-HCV-core protein, and $PTD_1$-$J_1$, were respectively spotted onto PVDF membranes. The membranes were blocked by 5% skim milk in TBSN (25 mM Tris-HCl, pH 7.4, 150 mM NaCl, 0.02% Tween 20) for 1 hour. After 4 washes with TBSN, the membranes were incubated with mouse anti-serum overnight at a dilution 1:1000, unbound primary antibodies (Ab) removed from the membrane by 4 washes with TBSN, and incubated with HRP-conjugated goat anti-mouse secondary Ab (2000× dilution) for 4 hours. The labeled proteins on washed membrane were detected by chemiluminescence according to manufacturer's instructions (Pierce).

Figure 11:
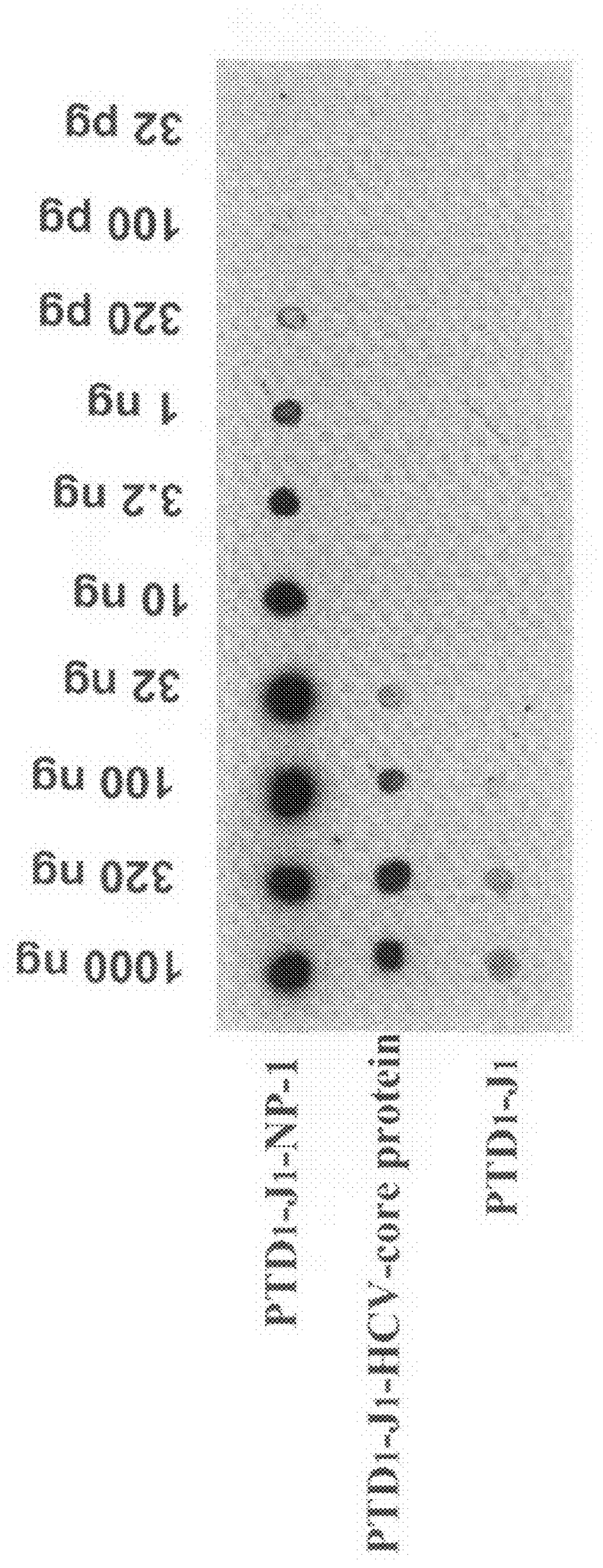
FIG. 11 is a photograph showing the result of a Dot blot analysis.

As shown in FIG. 11, the mouse anti-serum, at 1000× dilution, was highly sensitive in detecting the antigen $PTD_1$-$J_1$-NP-1, less sensitive to $PTD_1$-$J_1$-HCV-core protein, and even less sensitive to $PTD_1$-$J_1$. The antigen $PTD_1$-$J_1$-NP-1 in amounts as small as 320 pg was detectable by the mouse anti-serum (1000× dilution). On the other hand, at least 32 ng of $PTD_1$-$J_1$-HCV-core protein was needed to produce an equivalently weak signal. The signal produced by interacting with $PTD_1$-$J_1$ was very weak even at the amounts as high as 100 ng. This indicates that more than 99% of anti-serum interacted with the target protein NP-1, and less than 1% interacted with $PTD_1$-$J_1$-HCV-core protein and $PTD_1$-$J_1$. Therefore, the recombinant protein $PTD_1$-$J_1$-NP-1 was able to raise a high titer of antibody specific against the target protein NP-1.

Example 12

Enhanced Solubility of Recombinant Protein

Construction of pET32b-cIGF-I. To compare the solubility of a target protein with the protein fused to a J domain, the construct pET32b-cIGF-I was generated by inserting the EcoRI/XhoI DNA fragment of pET22b-$PTD_1$-$J_1$-cIGF-I into the same restriction enzyme sites of pET32b to form a pET32b-cIGF-I expression vector.

Expression of Target Protein. Recombinant proteins were expressed in *E. coli* cultures containing corresponding expression plasmids. In brief, the colony resistant to ampicillin and chloramphenicol was cultured and amplified in TYD medium (10 g trypton, 20 g yeast extract, 5 g NaCl, 2 g Dextrose per liter, pH 7.2) at 37° C. Once the bacterial density reached 0.3±0.1 $OD_{600}$, the incubation temperature of bacterial cultures were set at 37° C., 30° C., 25° C., 20° C. and 15° C., respectively, and then isopropylthio-β-D-galactoside (IPTG; Promega, USA) was added into the cultures at a final concentration of 1 mM, and induced protein expression for 3, 4, 5, 6 hrs, and overnight, respectively, in a rotating incubator shaken at 225 rpm. After the IPTG induction, the cells were collected by centrifugation at 5,000×g for 10 min, washed once with PBS and resuspended in PBS for homogenization by sonication. The sonicated lysates were centrifuged at 15,000×g for 30 min. Supernatants (soluble fractions) were collected. The pellets (insoluble fractions) were washed once with PBS to remove residual soluble proteins before re-suspending in PBS to obtain the insoluble fractions, which included protein inclusion bodies. About 30 μl of each fraction from the amount equivalent of 0.5 $OD_{600}$ unit of *E. coli* cells were loaded into each well of the gel. The gel was stained with Coomassie brilliant blue R-250 and scanned by laser densitometer (Personal Densitometer SI, Molecular Dynamics).

Figure 12A:
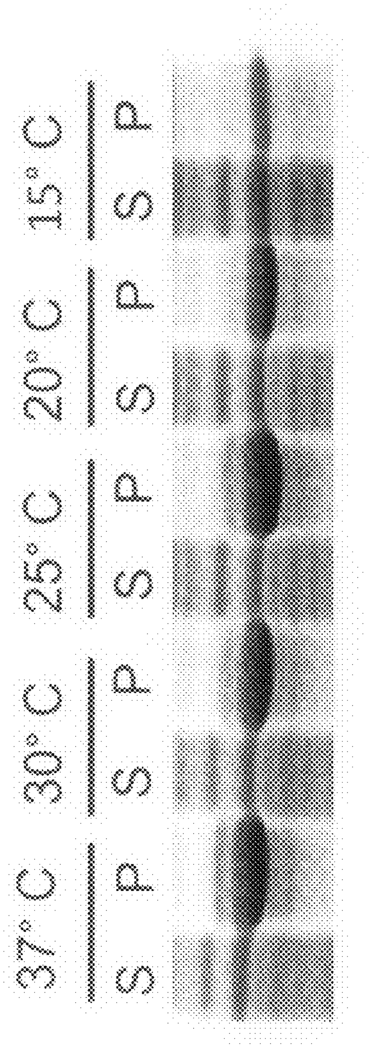
FIG. 12A is a photograph of SDS-PAGE gel electrophoresis. "S" stands for supernatant; "P" stands for insoluble pellet fraction. Prior to being loaded into the gel, the insoluble pellet was dissolved in SDS-PAGE loading buffer.
Figure 12B:
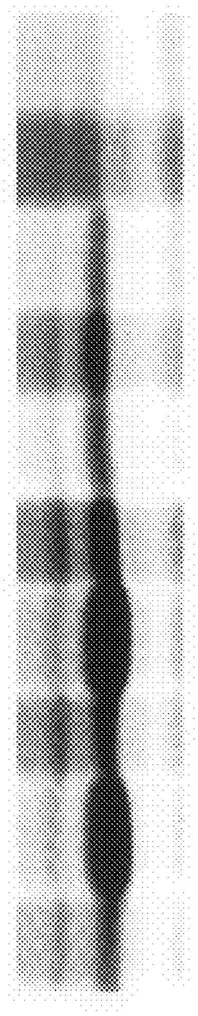
FIG. 12B is a photograph of SDS-PAGE gel electrophoresis. The labels for lanes 1-10 are the same as FIG. 12A.

Results:

Expression of thioredoxin fusion protein of cIGF-I. The mature cIGF-I polypeptide (70 amino acid residues) contains 6 cysteines that make 3 disulfide bonds. This protein is very difficult to be expressed in *E. coli* in a soluble form. The pET32-series plasmids encodes a thioredoxin A, a disulfide bond isomerase, has been commonly used to improve the solubility of proteins. FIGS. 12A and 12B show the results of the SDS-PAGE gel electrophoresis of the soluble and insoluble sample fractions. As shown in FIG. 12A, thioredoxin-cIGF-I was found in both supernatant (S) and insoluble pellet (P) fractions, but most of the recombinant protein was in the pellete when the induction temperature was at from 37° C. to 20° C. The total amounts of the recombinant protein thioredoxin-cIGF-I produced (in S+P fractions) were similar when the induction temperature was at between 37° C. to 20° C., but declined dramatically at 15° C. These results indicated that thioredoxin fusion protein of cIGF-I expressed in *E. coli* host cells harboring the vector pET32b-cIGF-I was predominantly present in insoluble form. The weight ratios (S/S+P) of the soluble form (S) fusion protein versus the total fusion protein (soluble form plus insoluble form, S+P) for the recombinant protein thioredoxin A-cIGF-I were 6%, 8%, 7%, 7% and 65% at 37° C., 30° C., 25° C., 20° C., and 15° C., respectively (Table 9). Although the low temperature at 15° C. increased the percentage of soluble recombinant protein (i.e., solubility), the overall yield was lower.

Expression of J-Domain fusion protein of cIGF-I. Unlike thioredoxin fusion protein of cIGF-I, the weight ratios of soluble $PTD_1$-$J_1$-cIGF-I fusion protein increased dramatically as the induction temperature decreased from 37° C. to 15° C., as shown in FIG. 12B. The total amounts of the recombinant protein $PTD_1$-$J_1$-cIGF-I (S+P) reduced as the induction temperature was decreased from 37° C. to 20° C. Very little of $PTD_1$-$J_1$-cIGF-I fusion protein was detected at the induction temperature of 15° C. The amount of the soluble recombinant proteins expressed at various temperatures was calculated and expressed as weight ratio as shown in Table 9. The weight ratios (S/S+P) of the soluble form fusion protein (S) versus the total fusion protein (S+P) for fusion protein $PTD_1$-$J_1$-cIGF-I were 4%, 11%, 70%, 87% and 91% at 37° C., 30° C., 25° C., 20° C., and 15° C., respectively. The data in Table 9 indicates that at the temperature from 25° C. to 15° C., the weight ratio of soluble cIGF-I relative to the total proteins was significantly higher in the J-domain-containing expression system than in the tioredoxin-containing expression system.

TABLE 9

| Total fusion Protein | Soluble fusion protein | | | | |
|---|---|---|---|---|---|
| (% w/w, S/S+P) | 37° C. | 30° C. | 25° C. | 20° C. | 15° C. |
| $PTD_1$-$J_1$-cIGF-I | 4% | 11% | 70% | 87% | 91% |
| Thioredoxin A-cIGF-I | 6% | 8% | 7% | 7% | 65% |

J-domain Enhanced Solubility of Target Protein. The yields of the $PTD_1$-$J_1$-cIGF-I fusion protein in the soluble lysate fractions at different culture temperatures were measure as follows. The amount of $PTD_1$-$J_1$-cIGF-I and thioredoxin A-cIGF-I recombinant proteins in the soluble fractions relative to the total soluble lysate proteins was measured by scanning. The peak areas of the $PTD_1$-$J_1$-cIGF-I and thioredoxin A-cIGF-I recombinant protein (soluble fraction) relative to a constitutively expressed internal protein (an internal standard from the same soluble fraction) at different culture temperature were calculated and represented as "peak area ratio," as shown in Table 10. The data indicates that at the temperature from 37° C. to 20° C., the amounts of soluble cIGF-1 were significantly higher in the J-domain-containing expression system than in the thioredoxin-containing expression system.

Figure 13:
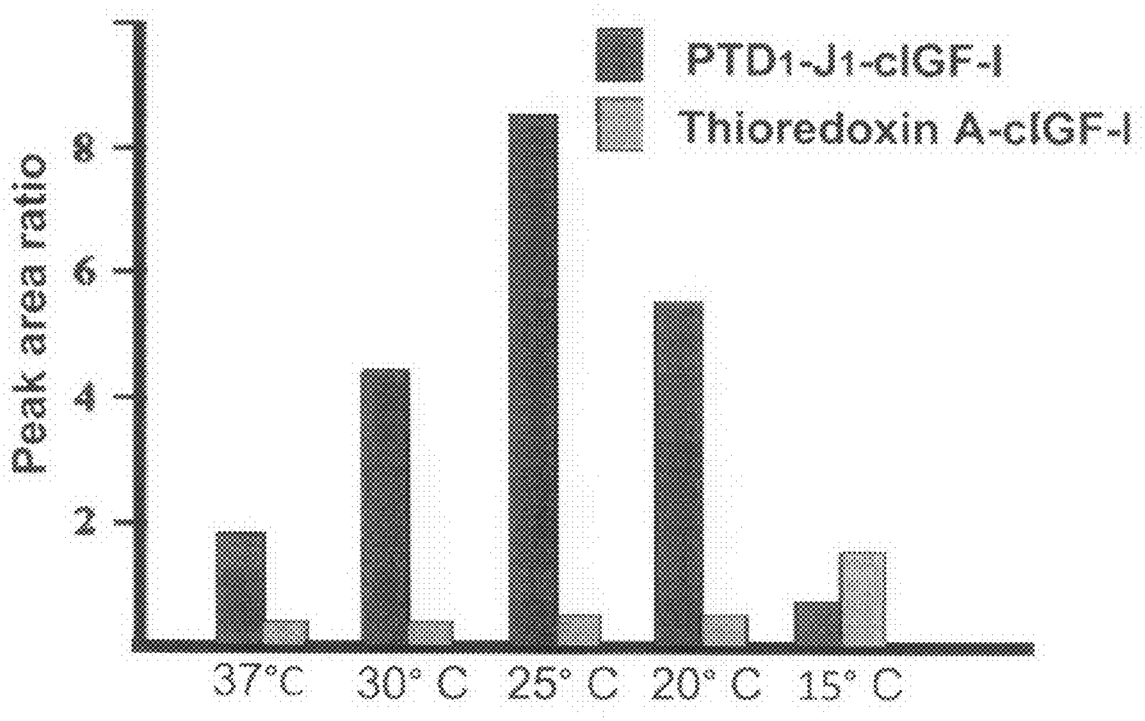
FIG. 13 is a chart showing the effects of the temperature on the recombinant protein expression. The peak area ratio represents the relative ratio of the recombinant proteins in the soluble fraction of *E. coli* cell lysate against a constitutively expressed internal protein.

Although the protein solubility was increased dramatically at the lower temperature (Table 9), the amount of soluble recombinant protein $PTD_1$-$J_1$-cIGF-decreased as the induction temperature was lowered to 20° C. or 15° C. (Table 10). This indicates that an optimal induction temperature for J-domain fused recombinant protein expression would need to be determined for each target protein expression. The estimated optimal culture temperature for expression of $PTD_1$-$J_1$-cIGF-I fusion protein was at about 25° C., as shown in FIG. 13.

TABLE 10

| Peak area ratio | 37° C. | 30° C. | 25° C. | 20° C. | 15° C. |
|---|---|---|---|---|---|
| $PTD_1$-$J_1$-cIGF-I | 1.8 | 4.4 | 8.5 | 5.5 | 0.7 |
| Thioredoxin A-cIGF-I | 0.4 | 0.4 | 0.5 | 0.5 | 1.5 |

Example 13

Enhanced Immunogenicity of Recombinant Protein

Haptoglobin α-chain contains antigenic motives located at N-peptide (amino acid residues 20 to 32) and C-peptide (amino acid residues 252 to 267). Neither the N-peptide nor the C-peptide of the haptoglobin α-chain by itself was able to elicit detectable antibodies. To increase their immunogenicities, a fusion polypeptide of N and C peptides, i.e., HpNC, was fused to the carboxyl terminal end of the chimeric gene $PTD_1$-$J_1$ and expressed as a recombinant $PTD_1$-$J_1$-HpNC peptide to raise a high titer of anti-serum in animals. The immunogenicity of the anti-serum was analyzed using SDS-PAGE gel electrophoresis and Western Blotting.

Immunization of Animals with Haptoglobin Fusion Polypeptide, HpNC.

The recombinant $PTD_1$-$J_1$-HpNC peptide was isolated to immune rats to raise antibodies against human haptoglobin using the following procedure. Each rat was injected subdermally with 500 μg recombinant polypeptide in 0.4 ml emulsified adjuvant. After three boosts, the rat serum was collected.

SDS-PAGE gel Analysis and Western Blotting. Each human serum sample (1 μl), in duplicate, with known haptoglobin phenotypes, Hp 1-1, Hp 2-1, and Hp 2-2, was loaded onto 15% SDS polyacryamide gel. After semi-dry electrotransfer and blocking, the PVDF membrane was charged with a 1500-fold diluted rat serum at room temperature for 2 hr followed by an application of a 2500-fold diluted HRP-coupled goat-anti-rat IgG antibody (A-9037, Sigma) at room temperature for 2 h. The signals were detected by chemilumiscence (Cat #34080, Pierce).

Figure 14A:
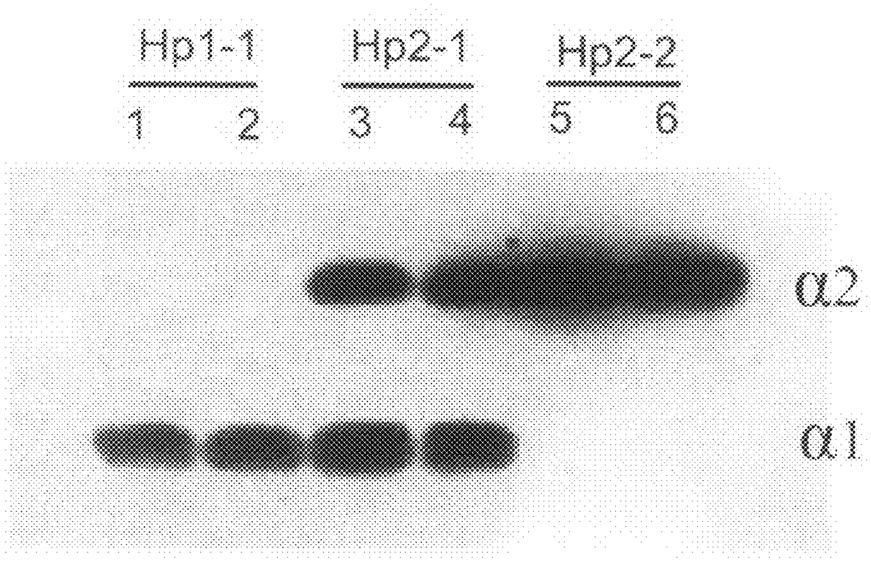
FIG. 14A is a photograph of SDS-PAGE gel electrophoresis.

Results:

There are two haptoglobin (Hp) α-chain alleles, Hp1 and Hp2, in human population. The exon 2 of the Hp1 gene is duplicated once in the Hp2 allele, and the apparent molecular weights of the secreted mature α1 and α2 peptide of haptoglobin were 14 kDa and 20 kDa by SDS PAGE, respectively (Rademacher & Steele 1987; Tseng et al. 2004). Human serum samples of known Hp 1-1, Hp 2-1, and Hp 2-2 phenotypes were utilized to test the rat anti-HpNC serum. The rat anti-HpNC serum could distinctly recognize 14 kDa α1 and 20 kDa α2 secreted forms of haptoglobin α-chain, as indicated in FIG. 14A.

Figure 14B:
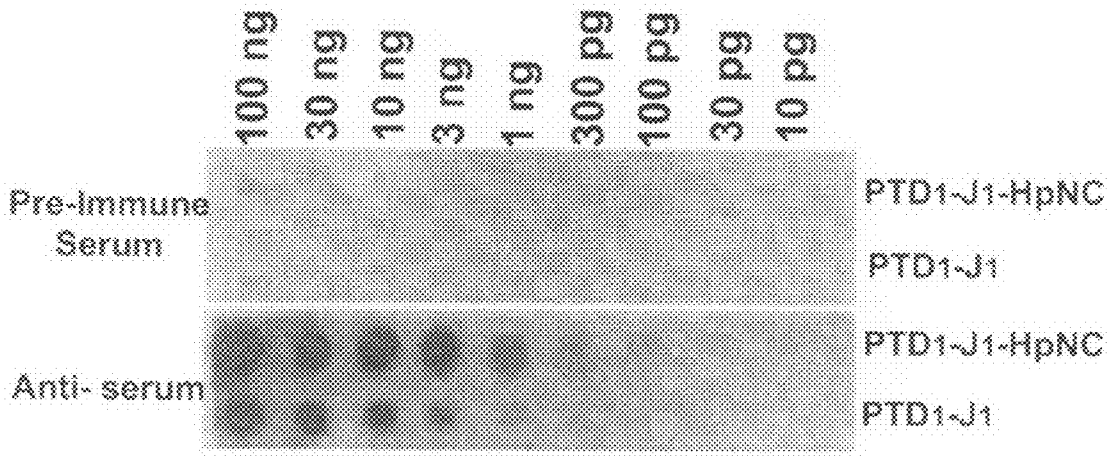
FIG. 14B is a photograph showing the result of a Dot blot analysis.

The immunogenicity of the $PTD_1$-$J_1$ peptide relative to the HpNC peptide was also assayed using dot blotting analyses. The pre-immune serum and rat anti-$PTD_1$-$J_1$-HpNC serum were utilized as primary antibodies in the immuno-blotting assay. Serially diluted amounts of recombinant polypeptides $PTD_1$-$J_1$-HpNC and $PTD_1$-$J_1$ were spotted on the PVDF membrane before subsequent incubations with rat pre-immune serum or rat anti-HpNC serum and followed by HRP-conjugated goat anti-rat IgG. As shown in FIG. 14B, the lowest detectable amount of $PTD_1$-$J_1$ and $PTD_1$-$J_1$-HpNC were 1 ng and 100 pg, respectively. That is, the HpNC region of the recombinant $PTD_1$-$J_1$-HpNC polypeptide was much more immunogenic than the accompanying $PTD_1$-$J_1$ region.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

REFERENCES

1. Fan C. Y., Lee S. and Cyr D. M. (2003) Mechanisms for regulation of Hsp70 function by Hsp40. *Cell Stress Chaperones,* 8, 309-16.
2. Genevaux P., Georgopoulos C. and Kelley W. L. (2007) The Hsp70 chaperone machines of *Escherichia coli:* a paradigm for the repartition of chaperone functions. *Mol Microbiol,* 66, 840-57.
3. Jones S. W., Christison R., Bundell K., Voyce C. J., Brockbank S. M., Newham P. and Lindsay M. A. (2005) Characterisation of cell-penetrating peptide-mediated peptide delivery. *Br J Pharmacol,* 145, 1093-102.
4. Kaplan I. M., Wadia J. S. and Dowdy S. F. (2005) Cationic TAT peptide transduction domain enters cells by macropinocytosis. *J Control Release,* 102, 247-53.
5. Ryu J., Han K., Park J. and Choi S. Y. (2003) Enhanced uptake of a heterologous protein with an HIV-1 Tat protein transduction domains (PTD) at both termini. *Mol Cells,* 16, 385-91.
6. Shaner L. and Morano K. A. (2007) All in the family: atypical Hsp70 chaperones are conserved modulators of Hsp70 activity. *Cell Stress Chaperones,* 12, 1-8.
7. Tilstra. J., Rehman. K. K., Hennon. T., Plevy., S. E., Clemens. P. and Robins. P. D. (2007) Protein transduction: identification, characterization and optimization. *Biochem Soc Trans.,* 35, 811-5.
8. Wadia J. S., Stan R. V. and Dowdy S. F. (2004) Transducible TAT-HA fusogenic peptide enhances escape of TAT-fusion proteins after lipid raft macropinocytosis. *Nat Med,* 10, 310-5.
9. Campbell K. S., Mullane K. P., Aksoy I. A., Stubdal H., Zalvide J., Pipas J. M., Silver P. A., Roberts T. M., Schaffhausen B. S., and DeCaprio J. A. (1997) DnaJ/hsp40 chaperone domain of SV40 large T antigen promotes efficient viral DNA replication. *Genes & Development* 11: 1098-1110.

SEQUENCE LISTING

```
<160> NUMBER OF SEQ ID NOS: 68

<210> SEQ ID NO 1
<211> LENGTH: 11
<212> TYPE: PRT
<213> ORGANISM: Human immunodeficiency virus
<220> FEATURE:
<223> OTHER INFORMATION: Human immunodeficiency virus Tat PTD1

<400> SEQUENCE: 1

Tyr Gly Arg Lys Lys Arg Arg Gln Arg Arg Arg
1               5                   10


<210> SEQ ID NO 2
<211> LENGTH: 33
<212> TYPE: DNA
<213> ORGANISM: Artificial Sequenece
<220> FEATURE:
<223> OTHER INFORMATION: Human immunodeficiency virus Tat PTD1

<400> SEQUENCE: 2

tatggtcgta agaaacgtcg tcagcgtcgt cgt                                 33


<210> SEQ ID NO 3
<211> LENGTH: 72
<212> TYPE: PRT
<213> ORGANISM: Homo sapiens
<220> FEATURE:
<223> OTHER INFORMATION: HSP40 J-domain (J1)

<400> SEQUENCE: 3

Gly Lys Asp Tyr Tyr Gln Thr Leu Gly Leu Ala Arg Gly Ala Ser Asp
1               5                   10                  15

Asp Glu Ile Lys Arg Ala Tyr Arg Arg Gln Ala Leu Arg Tyr His Pro
20                  25                  30

Asp Lys Asn Lys Glu Pro Arg Ala Glu Glu Lys Phe Lys Glu Ile Ala
35                  40                  45

Tyr Asp Val Leu Ser Asp Pro Arg Lys Arg Lys Arg Glu Ile Phe Asp
50                  55                  60

Arg Tyr Gly Glu Glu Gly Leu Lys
```

-continued 65 70

<210> SEQ ID NO 4
<211> LENGTH: 216
<212> TYPE: DNA
<213> ORGANISM: Artificial Sequenece
<220> FEATURE:
<223> OTHER INFORMATION: HSP40 J-domain (J1)-encoding sequence

<400> SEQUENCE: 4
ggtaaagatt actaccagac tcacggtctc gctcgtggtg catctgatga tgaaatcaaa 60
cgtgcttacc gtcgtcaggc actgcgttac catccagaca aaaacaaaga accgcgtgca 120
gaagagaaat tcaaagagat cgcagaagca tacgacgttc tgagcgatcc acgtaaacgt 180
gaaatctccg accgttacgg tgaagaaggt ctgaaa 216

<210> SEQ ID NO 5
<211> LENGTH: 39
<212> TYPE: DNA
<213> ORGANISM: Artificial Sequenece
<220> FEATURE:
<223> OTHER INFORMATION: Forward primer PTD1 f for synthesis of PTD1

<400> SEQUENCE: 5
tatgtatggt cgtaagaaac gtcgtcagcg tcgtcgtgg 39

<210> SEQ ID NO 6
<211> LENGTH: 41
<212> TYPE: DNA
<213> ORGANISM: Artificial Sequenece
<220> FEATURE:
<223> OTHER INFORMATION: Forward primer PTD1 r for synthesis of PTD1

<400> SEQUENCE: 6
gatcccacga cgacgctgac gacgtttctt acgaccatac a 41

<210> SEQ ID NO 7
<211> LENGTH: 39
<212> TYPE: DNA
<213> ORGANISM: Artificial Sequenece
<220> FEATURE:
<223> OTHER INFORMATION: Forward primer J1 nBF1 for synthesis of HSP40
J-domain

<400> SEQUENCE: 7
tggatcctgg gtaaagatta ctaccagact cacggtctc 39

<210> SEQ ID NO 8
<211> LENGTH: 48
<212> TYPE: DNA
<213> ORGANISM: Artificial Sequenece
<220> FEATURE:
<223> OTHER INFORMATION: Forward primer nF2 for synthesis of HSP40
J-domain

<400> SEQUENCE: 8
tactaccaga ctcacggtct cgctcgtggt gcatctgatg atgaaatc 48

<210> SEQ ID NO 9
<211> LENGTH: 48
<212> TYPE: DNA
<213> ORGANISM: Artificial Sequenece
<220> FEATURE:
<223> OTHER INFORMATION: Forward primer F3 for synthesis of HSP40
J-domain -continued

<400> SEQUENCE: 9
ggtgcatctg atgatgaaat caaacgtgct taccgtcgtc aggcactg 48

<210> SEQ ID NO 10
<211> LENGTH: 48
<212> TYPE: DNA
<213> ORGANISM: Artificial Sequenece
<220> FEATURE:
<223> OTHER INFORMATION: Forward primer F4 for synthesis of HSP40
J-domain

<400> SEQUENCE: 10
gcttaccgtc gtcaggcact gcgttaccat ccagacaaaa acaaagaa 48

<210> SEQ ID NO 11
<211> LENGTH: 45
<212> TYPE: DNA
<213> ORGANISM: Artificial Sequenece
<220> FEATURE:
<223> OTHER INFORMATION: Forward primer F5 for synthesis of HSP40
J-domain

<400> SEQUENCE: 11
taccatccag acaaaaacaa agaaccgggt gcagaagaga aattc 45

<210> SEQ ID NO 12
<211> LENGTH: 48
<212> TYPE: DNA
<213> ORGANISM: Artificial Sequenece
<220> FEATURE:
<223> OTHER INFORMATION: Forward primer F6 for synthesis of HSP40
J-domain

<400> SEQUENCE: 12
ccgggtgcag aagagaaatt caaagagatc gcagaagcat acgacgtt 48

<210> SEQ ID NO 13
<211> LENGTH: 36
<212> TYPE: DNA
<213> ORGANISM: Artificial Sequenece
<220> FEATURE:
<223> OTHER INFORMATION: Reverse primer EcoR1 R1 for synthesis of HSP40
J-domain

<400> SEQUENCE: 13
cgaattcgca ccaccagaac cacctttcag accttc 36

<210> SEQ ID NO 14
<211> LENGTH: 48
<212> TYPE: DNA
<213> ORGANISM: Artificial Sequenece
<220> FEATURE:
<223> OTHER INFORMATION: Reverse primer R2 for synthesis of HSP40
J-domain

<400> SEQUENCE: 14
agaaccacct ttcagacctt cttcaccgta acggtcgaag atttcacg 48

<210> SEQ ID NO 15
<211> LENGTH: 48
<212> TYPE: DNA
<213> ORGANISM: Artificial Sequenece
<220> FEATURE:
<223> OTHER INFORMATION: Reverse primer R3 for synthesis of HSP40
J-domain

<400> SEQUENCE: 15

-continued

```
gtaacggtcg aagatttcac gtttacgtgg atcgctcaga acgtcgta                48


<210> SEQ ID NO 16
<211> LENGTH: 36
<212> TYPE: DNA
<213> ORGANISM: Artificial Sequenece
<220> FEATURE:
<223> OTHER INFORMATION: Reverse primer R4 for synthesis of HSP40
      J-domain

<400> SEQUENCE: 16

tggatcgctc agaacgtcgt atgcttctgc gatctc                             36


<210> SEQ ID NO 17
<211> LENGTH: 171
<212> TYPE: DNA
<213> ORGANISM: Artificial Sequenece
<220> FEATURE:
<223> OTHER INFORMATION: Human HSPA1A peptide I-encoding sequence

<400> SEQUENCE: 17

agcagcagca cccaggcgag cctggaaatt gatagcctgt ttgaaggcat tgatttttat     60

accagcatta cccgtgcgcg ttttgaagaa ctgtgcagcg atctgtttcg tagcaccctg    120

gaaccggtgg aaaaagcgct gcgtgatgcg aaactggata aagcgcagat t            171


<210> SEQ ID NO 18
<211> LENGTH: 57
<212> TYPE: PRT
<213> ORGANISM: Homo sapiens
<220> FEATURE:
<223> OTHER INFORMATION: Human HSPA1A peptide I

<400> SEQUENCE: 18

Ser Ser Ser Thr Gln Ala Ser Leu Glu Ile Asp Ser Leu Phe Glu Gly
1               5                   10                  15

Ile Asp Phe Tyr Thr Ser Ile Thr Arg Ala Arg Phe Glu Glu Leu Cys
20                  25                  30

Ser Asp Leu Phe Arg Ser Thr Leu Glu Pro Val Glu Lys Ala Leu Arg
35                  40                  45

Asp Ala Lys Leu Asp Lys Ala Gln Ile
50                  55


<210> SEQ ID NO 19
<211> LENGTH: 49
<212> TYPE: DNA
<213> ORGANISM: Artificial Sequenece
<220> FEATURE:
<223> OTHER INFORMATION: Forward primer RI-I-f1 for synthesis of
      HSPA1A peptide I

<400> SEQUENCE: 19

gaattctagc agcagcaccc aggcgagcct ggaaattgat agcctgttt               49


<210> SEQ ID NO 20
<211> LENGTH: 48
<212> TYPE: DNA
<213> ORGANISM: Artificial Sequenece
<220> FEATURE:
<223> OTHER INFORMATION: Forward primer I-f2 for synthesis of
      HSPA1A peptide I

<400> SEQUENCE: 20

agcctggaaa ttgatagcct gtttgaaggc attgattttt ataccagc                48
```

-continued

<210> SEQ ID NO 21
<211> LENGTH: 49
<212> TYPE: DNA
<213> ORGANISM: Artificial Sequenece
<220> FEATURE:
<223> OTHER INFORMATION: Forward primer I-f3 for synthesis of
HSPA1A peptide I

<400> SEQUENCE: 21
gtttgaaggc attgattttt ataccagcat tacccgtgcg cgttttgaa 49

<210> SEQ ID NO 22
<211> LENGTH: 49
<212> TYPE: DNA
<213> ORGANISM: Artificial Sequenece
<220> FEATURE:
<223> OTHER INFORMATION: Reverse primer I-r3 for synthesis of
HSPA1A peptide I

<400> SEQUENCE: 22
gggtgctacg aaacagatcg ctgcacagtt cttcaaaacg cgcacgggt 49

<210> SEQ ID NO 23
<211> LENGTH: 49
<212> TYPE: DNA
<213> ORGANISM: Artificial Sequenece
<220> FEATURE:
<223> OTHER INFORMATION: Reverse primer I-r2 for synthesis of
HSPA1A peptide I

<400> SEQUENCE: 23
catcacgcag cgctttttcc accggttcca gggtgctacg aaacagatc 49

<210> SEQ ID NO 24
<211> LENGTH: 48
<212> TYPE: DNA
<213> ORGANISM: Artificial Sequenece
<220> FEATURE:
<223> OTHER INFORMATION: Reverse primer Xho-I-r1 for synthesis of
HSPA1A peptide I

<400> SEQUENCE: 24
ctcgagaatc tgcgctttat ccagtttcgc atcacgcagc gctttttc 48

<210> SEQ ID NO 25
<211> LENGTH: 183
<212> TYPE: DNA
<213> ORGANISM: Artificial Sequenece
<220> FEATURE:
<223> OTHER INFORMATION: Human HSPA1A peptide II-encoding sequence

<400> SEQUENCE: 25
aacgtaaccg ctactgacaa atccactggt aaagctaaca agatcaccat caccaacgac 60
aaaggtcgtc tgtccaagga agagatcgag cgtatggttc aggaagctga aaagtacaag 120
gctgaagacg aagttcagcg tgaacgtgtt tccgctaaga acgctctgga atcctacgct 180
ttc 183

<210> SEQ ID NO 26
<211> LENGTH: 61
<212> TYPE: PRT
<213> ORGANISM: Homo sapiens
<220> FEATURE:
<223> OTHER INFORMATION: Human HSPA1A peptide II -continued

<400> SEQUENCE: 26

```
Asn Val Thr Ala Thr Asp Lys Ser Thr Gly Lys Ala Asn Lys Ile Thr
1               5                   10                  15

Ile Thr Asn Asp Lys Gly Arg Leu Ser Lys Glu Glu Ile Glu Arg Met
20                  25                  30

Val Gln Glu Ala Glu Lys Tyr Lys Ala Glu Asp Glu Val Gln Arg Glu
35                  40                  45

Arg Val Ser Ala Lys Asn Ala Leu Glu Ser Tyr Ala Phe
50                  55                  60
```

<210> SEQ ID NO 27
<211> LENGTH: 49
<212> TYPE: DNA
<213> ORGANISM: Artificial Sequenece
<220> FEATURE:
<223> OTHER INFORMATION: Forward primer RI-II-f1 for synthesis of HSPA1A peptide II

<400> SEQUENCE: 27
gaattctaac gtaaccgcta ctgacaaatc cactggtaaa gctaacaag 49

<210> SEQ ID NO 28
<211> LENGTH: 49
<212> TYPE: DNA
<213> ORGANISM: Artificial Sequenece
<220> FEATURE:
<223> OTHER INFORMATION: Forward primer II-f2 for synthesis of HSPA1A peptide II

<400> SEQUENCE: 28
tccactggta aagctaacaa gatcaccatc accaacgaca aaggtcgtc 49

<210> SEQ ID NO 29
<211> LENGTH: 49
<212> TYPE: DNA
<213> ORGANISM: Artificial Sequenece
<220> FEATURE:
<223> OTHER INFORMATION: Forward primer II-f3 for synthesis of HSPA1A peptide II

<400> SEQUENCE: 29
atcaccaacg acaaaggtcg tctgtccaag gaagagatcg agcgtatgg 49

<210> SEQ ID NO 30
<211> LENGTH: 45
<212> TYPE: DNA
<213> ORGANISM: Artificial Sequenece
<220> FEATURE:
<223> OTHER INFORMATION: Forward primer II-f4 for synthesis of HSPA1A peptide II

<400> SEQUENCE: 30
aaggaagaga tcgagcgtat ggttcaggaa gctgaaaagt acaag 45

<210> SEQ ID NO 31
<211> LENGTH: 46
<212> TYPE: DNA
<213> ORGANISM: Artificial Sequenece
<220> FEATURE:
<223> OTHER INFORMATION: Reverse primer II-r3 for synthesis of HSPA1A peptide II

<400> SEQUENCE: 31
acgctgaact tcgtcttcag ccttgtactt ttcagcttcc tgaacc 46

-continued

```
<210> SEQ ID NO 32
<211> LENGTH: 45
<212> TYPE: DNA
<213> ORGANISM: Artificial Sequenece
<220> FEATURE:
<223> OTHER INFORMATION: Reverse primer II-r2 for synthesis of
      HSPA1A peptide II

<400> SEQUENCE: 32

agcgttctta gcggaaacac gttcacgctg aacttcgtct tcagc                   45


<210> SEQ ID NO 33
<211> LENGTH: 49
<212> TYPE: DNA
<213> ORGANISM: Artificial Sequenece
<220> FEATURE:
<223> OTHER INFORMATION: Reverse primer Xho-II-r1 for synthesis of
      HSPA1A peptide II

<400> SEQUENCE: 33

ctcgaggaaa gcgtaggatt ccagagcgtt cttagcggaa acacgttca               49


<210> SEQ ID NO 34
<211> LENGTH: 183
<212> TYPE: DNA
<213> ORGANISM: Artificial Sequenece
<220> FEATURE:
<223> OTHER INFORMATION: Human HSPA1A peptide III-encoding sequence

<400> SEQUENCE: 34

gaagatgaag gcctgaaagg caaaattagc gaagcggata agaaaaaggt gctggataaa     60

tgccaggaag tgattagctg gctggatgcg aacaccctgg cggaaaaaga tgaatttgaa    120

cataaacgta aagaactgga acaggtgtgc aacccgatta ttagcggcct gtatcagggc    180

gcg                                                                  183


<210> SEQ ID NO 35
<211> LENGTH: 61
<212> TYPE: PRT
<213> ORGANISM: Homo sapiens
<220> FEATURE:
<223> OTHER INFORMATION: Human HSPA1A peptide III

<400> SEQUENCE: 35

Glu Asp Glu Gly Leu Lys Gly Lys Ile Ser Glu Ala Asp Lys Lys Lys
1               5                   10                  15

Val Leu Asp Lys Cys Gln Glu Val Ile Ser Trp Leu Asp Ala Asn Thr
20                  25                  30

Leu Ala Glu Lys Asp Glu Phe Glu His Lys Arg Lys Glu Leu Glu Gln
35                  40                  45

Val Cys Asn Pro Ile Ile Ser Gly Leu Tyr Gln Gly Ala
50                  55                  60


<210> SEQ ID NO 36
<211> LENGTH: 46
<212> TYPE: DNA
<213> ORGANISM: Artificial Sequenece
<220> FEATURE:
<223> OTHER INFORMATION: Forward primer RI-III-f1 for synthesis of
      HSPA1A peptide III

<400> SEQUENCE: 36

gaattctgaa gatgaaggcc tgaaaggcaa aattagcgaa gcggat                  46
```

-continued

<210> SEQ ID NO 37
<211> LENGTH: 48
<212> TYPE: DNA
<213> ORGANISM: Artificial Sequenece
<220> FEATURE:
<223> OTHER INFORMATION: Forward primer III-f2 for synthesis of
HSPA1A peptide III

<400> SEQUENCE: 37
ggcaaaatta gcgaagcgga taagaaaaag gtgctggata aatgccag 48

<210> SEQ ID NO 38
<211> LENGTH: 49
<212> TYPE: DNA
<213> ORGANISM: Artificial Sequenece
<220> FEATURE:
<223> OTHER INFORMATION: Forward primer III-f3 for synthesis of
HSPA1A peptide III

<400> SEQUENCE: 38
ggtgctggat aaatgccagg aagtgattag ctggctggat gcgaacacc 49

<210> SEQ ID NO 39
<211> LENGTH: 49
<212> TYPE: DNA
<213> ORGANISM: Artificial Sequenece
<220> FEATURE:
<223> OTHER INFORMATION: Forward primer III-f4 for synthesis of
HSPA1A peptide III

<400> SEQUENCE: 39
gctggatgcg aacaccctgg cggaaaaaga tgaatttgaa cataaacgt 49

<210> SEQ ID NO 40
<211> LENGTH: 45
<212> TYPE: DNA
<213> ORGANISM: Artificial Sequenece
<220> FEATURE:
<223> OTHER INFORMATION: Reverse primer III-r3 for synthesis of
HSPA1A peptide III

<400> SEQUENCE: 40
ttccagttct ttacgtttat gttcaaattc atcttttttcc gccag 45

<210> SEQ ID NO 41
<211> LENGTH: 48
<212> TYPE: DNA
<213> ORGANISM: Artificial Sequenece
<220> FEATURE:
<223> OTHER INFORMATION: Reverse primer III-r2 for synthesis of
HSPA1A peptide III

<400> SEQUENCE: 41
cgggttgcac acctgttcca gttctttacg tttatgttca aattcatc 48

<210> SEQ ID NO 42
<211> LENGTH: 48
<212> TYPE: DNA
<213> ORGANISM: Artificial Sequenece
<220> FEATURE:
<223> OTHER INFORMATION: Reverse primer III-r1 for synthesis of
HSPA1A peptide III

<400> SEQUENCE: 42
ctcgagcgcg ccctgataca ggccgctaat aatcgggttg cacacctg 48

-continued

```
<210> SEQ ID NO 43
<211> LENGTH: 210
<212> TYPE: DNA
<213> ORGANISM: Artificial Sequenece
<220> FEATURE:
<223> OTHER INFORMATION: chicke IGF-1 encoding sequence

<400> SEQUENCE: 43

ggtccagaaa ccctgtgtgg tgcagaactg gttgatgcac tgcagttcgt gtgtggtgat     60

cgtggtttct acttcagcaa accgactggt tatggtagct ctagccgtcg tctgcatcac    120

aaaggtattg tggatgaatg ttgctttcag agctgtgatc tgcgtcgtct ggaaatgtac    180

tgtgcaccaa tcaaaccacc gaaaagcgca                                     210


<210> SEQ ID NO 44
<211> LENGTH: 70
<212> TYPE: PRT
<213> ORGANISM: Gallus gallus
<220> FEATURE:
<223> OTHER INFORMATION: chicke IGF-1

<400> SEQUENCE: 44

Gly Pro Glu Thr Leu Cys Gly Ala Glu Leu Val Asp Ala Leu Gln Phe
1               5                   10                  15

Val Cys Gly Asp Arg Gly Phe Tyr Phe Ser Lys Pro Thr Gly Tyr Gly
20                  25                  30

Ser Ser Ser Ala Ala Leu His His Lys Gly Ile Val Asp Glu Cys Cys
35                  40                  45

Phe Gln Ser Cys Asp Leu Arg Arg Leu Glu Met Tyr Cys Ala Pro Ile
50                  55                  60

Lys Pro Pro Lys Ser Ala
65                  70


<210> SEQ ID NO 45
<211> LENGTH: 58
<212> TYPE: DNA
<213> ORGANISM: Artificial Sequenece
<220> FEATURE:
<223> OTHER INFORMATION: Forward primer RI-F1 new for synthesis of
      cIGF-I

<400> SEQUENCE: 45

gaattctggt ccagaaaccc tgtgtggtgc agaactggtt gatgcactgc agttcgtg       58


<210> SEQ ID NO 46
<211> LENGTH: 48
<212> TYPE: DNA
<213> ORGANISM: Artificial Sequenece
<220> FEATURE:
<223> OTHER INFORMATION: Forward primer F2 for synthesis of cIGF-I

<400> SEQUENCE: 46

gaactggttg atgcactgca gttcgtgtgt ggtgatcgtg gtttctac                 48


<210> SEQ ID NO 47
<211> LENGTH: 51
<212> TYPE: DNA
<213> ORGANISM: Artificial Sequenece
<220> FEATURE:
<223> OTHER INFORMATION: Forward primer F3 for synthesis of cIGF-I

<400> SEQUENCE: 47

ggtgatcgtg gtttctactt cagcaaaccg actggttatg gtagctctag c              51
```

-continued

<210> SEQ ID NO 48
<211> LENGTH: 49
<212> TYPE: DNA
<213> ORGANISM: Forward primer F4 for synthesis of cIGF-I
<220> FEATURE:
<223> OTHER INFORMATION: oligonucleotides

<400> SEQUENCE: 48
ggttatggta gctctagccg tcgtctgcat cacaaaggta ttgtggatg 49

<210> SEQ ID NO 49
<211> LENGTH: 50
<212> TYPE: DNA
<213> ORGANISM: Artificial Sequenece
<220> FEATURE:
<223> OTHER INFORMATION: Forward primer F5 for synthesis of cIGF-I

<400> SEQUENCE: 49
cacaaaggta ttgtggatga atgttgcttt cagagctgtg atctgcgtcg 50

<210> SEQ ID NO 50
<211> LENGTH: 45
<212> TYPE: DNA
<213> ORGANISM: Artificial Sequenece
<220> FEATURE:
<223> OTHER INFORMATION: Reverse primer R2 for synthesis of cIGF-I

<400> SEQUENCE: 50
gattggtgca cagtacattt ccagacgacg cagatcacag ctctg 45

<210> SEQ ID NO 51
<211> LENGTH: 46
<212> TYPE: DNA
<213> ORGANISM: Artificial Sequenece
<220> FEATURE:
<223> OTHER INFORMATION: Reverse primer Xho-R1 for synthesis of cIGF-I

<400> SEQUENCE: 51
ctcgagtgcg cttttcggtg gtttgattgg tgcacagtac atttcc 46

<210> SEQ ID NO 52
<211> LENGTH: 489
<212> TYPE: DNA
<213> ORGANISM: Artificial Sequenece
<220> FEATURE:
<223> OTHER INFORMATION: Avian Influenza HA (H5) RBD-encoding sequence

<400> SEQUENCE: 52
aaacacctat tgagcagaat aaaccatttt gagaaaattc agatcatccc caaaagttct 60
tggtccagtc atgaagcctc attaggggtg agctcagcat gtccatacca gggaaagtcc 120
tcctttttca gaaatgtggt atggcttatc aaaaagaaca gtacataccc aacaataaag 180
aggagctaca ataataccaa ccaagaagat cttttggtac tgtgggggat tcaccatcct 240
aatgatgcgg cagagcagac aaagctctat caaaacccaa ccacctatat ttccgttggg 300
acatcaacac taaaccagag attggtacca agaatagcta ctagatccga agtaaacggg 360
caaagtggaa ggatggagtt cttctggaca attttaaaac cgaatgatgc aatcaacttc 420
gagagtaatg gaaatttcat tgctccagaa tatgcataca aaattgtcaa gaaaggggac 480
tcaacaatt 489

<210> SEQ ID NO 53
<211> LENGTH: 163

-continued

<212> TYPE: PRT
<213> ORGANISM: Avian Influenza virus HA subtype H5
<220> FEATURE:
<223> OTHER INFORMATION: Avian Influenza HA (H5) RBD

<400> SEQUENCE: 53

Lys His Leu Leu Ser Arg Ile Asn His Phe Glu Lys Ile Gln Ile Ile
1               5                   10                  15

Pro Lys Ser Ser Trp Ser Ser His Glu Ala Ser Leu Gly Val Ser Ser
20                  25                  30

Ala Cys Pro Tyr Gln Gly Lys Ser Ser Phe Phe Arg Asn Val Val Trp
35                  40                  45

Leu Ile Lys Lys Asn Ser Thr Tyr Pro Thr Ile Lys Arg Ser Tyr Asn
50                  55                  60

Asn Thr Asn Gln Glu Asp Leu Leu Val Leu Trp Gly Ile His His Pro
65                  70                  75                  80

Asn Asp Ala Ala Glu Gln Thr Lys Leu Tyr Gln Asn Pro Thr Thr Tyr
85                  90                  95

Ile Ser Val Gly Thr Ser Thr Leu Asn Gln Arg Leu Val Pro Arg Ile
100                 105                 110

Ala Thr Arg Ser Glu Val Asn Gly Gln Ser Gly Arg Met Glu Phe Phe
115                 120                 125

Trp Thr Ile Leu Lys Pro Asn Asp Ala Ile Asn Phe Glu Ser Asn Gly
130                 135                 140

Asn Phe Ile Ala Pro Glu Tyr Ala Tyr Lys Ile Val Lys Lys Gly Asp
145                 150                 155                 160

Ser Thr Ile

<210> SEQ ID NO 54
<211> LENGTH: 32
<212> TYPE: DNA
<213> ORGANISM: Artificial Sequenece
<220> FEATURE:
<223> OTHER INFORMATION: Forward primer RI HA-RBD f for synthesis of avian influenza HA RBD

<400> SEQUENCE: 54
tgaattcgaa acacctattg agcagaataa ac                                32

<210> SEQ ID NO 55
<211> LENGTH: 31
<212> TYPE: DNA
<213> ORGANISM: Artificial Sequenece
<220> FEATURE:
<223> OTHER INFORMATION: Reverse primer Xho HA-RBD r for synthesis of avian influenza HA RBD

<400> SEQUENCE: 55
tctcgagaat tgttgagtcc cctttcttga c                                 31

<210> SEQ ID NO 56
<211> LENGTH: 573
<212> TYPE: DNA
<213> ORGANISM: Artificial Sequenece
<220> FEATURE:
<223> OTHER INFORMATION: Hepatitis C virus core protein-encoding sequence

<400> SEQUENCE: 56
atgagcacaa atcctaaacc tcaaagaaaa accaaaagaa acaccaaccg tcgcccagaa      60
gacgttaagt tcccgggcgg cggccagatc gttggcggag tatacttgtt gccgcgcagg     120

-continued

```
ggccccaggt tgggtgtgcg cacgacaagg aaaacttcgg agcggtccca gccacgtggg    180

agacgccagc ccatccccaa agatcggcgc tccactggca aggcctgggg aaaaccaggt    240

cgcccctggc ccctatatgg gaatgaggga ctcggctggg caggatggct cctgtccccc    300

cgaggctctc gcccctcctg gggccccact gacccccggc ataggtcgcg caacgtgggt    360

aaagtcatcg acaccctaac gtgtggcttt gccgacctca tggggtacat ccccgtcgta    420

ggcgccccgc ttagtggcgc cgccagagct gtcgcgcacg gcgtgagagt cctggaggac    480

ggggttaatt atgcaacagg gaacctaccc ggtttcccct tttctatctt cttgctggcc    540

ctgttgtcct gcatcaccgt tccggtctct gct                                573


<210> SEQ ID NO 57
<211> LENGTH: 191
<212> TYPE: PRT
<213> ORGANISM: Hepatitis C virus
<220> FEATURE:
<223> OTHER INFORMATION: Hepatitis C virus core protein

<400> SEQUENCE: 57

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
20                  25                  30

Gly Val Tyr Leu Leu Pro Arg Arg Gly Pro Arg Leu Gly Val Arg Thr
35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
85                  90                  95

Leu Leu Ser Pro Arg Gly Ser Arg Pro Ser Trp Gly Pro Thr Asp Pro
100                 105                 110

Arg His Arg Ser Arg Asn Val Gly Lys Val Ile Asp Thr Leu Thr Cys
115                 120                 125

Gly Phe Ala Asp Leu Met Gly Tyr Ile Pro Val Val Gly Ala Pro Leu
130                 135                 140

Ser Gly Ala Ala Arg Ala Val Ala His Gly Val Arg Val Leu Leu Asp
145                 150                 155                 160

Gly Val Asn Tyr Ala Thr Gly Asn Leu Pro Gly Phe Pro Phe Ser Ile
165                 170                 175

Phe Leu Leu Ala Leu Leu Ser Cys Ile Thr Val Pro Val Ser Ala
180                 185                 190


<210> SEQ ID NO 58
<211> LENGTH: 30
<212> TYPE: DNA
<213> ORGANISM: Artificial Sequenece
<220> FEATURE:
<223> OTHER INFORMATION: Forward primer RI-Core f for HCV-core protein

<400> SEQUENCE: 58

tgaattcgat gagcacaaat cctaaacctc                                     30


<210> SEQ ID NO 59
<211> LENGTH: 28
<212> TYPE: DNA
```

-continued

<213> ORGANISM: Artificial Sequenece
<220> FEATURE:
<223> OTHER INFORMATION: Reverse primer Xho-Core r for for HCV-core protein

<400> SEQUENCE: 59
tctcgagagc agagaccgga acggtgat 28

<210> SEQ ID NO 60
<211> LENGTH: 105
<212> TYPE: DNA
<213> ORGANISM: Artifical Sequence
<220> FEATURE:
<223> OTHER INFORMATION: Fusion gene encoding Human Haptoglobin Fusion Polypeptide HpNC

<400> SEQUENCE: 60
gatagcggta acgatgtgac cgatattgcg gatgatggtg gtagcggtgg tcgtcattat 60
gaaggtagca ccgttccgga gaagaaaacc ccaaagagcg gtggt 105

<210> SEQ ID NO 61
<211> LENGTH: 35
<212> TYPE: PRT
<213> ORGANISM: Homo Sapiens
<220> FEATURE:
<223> OTHER INFORMATION: Human Haptoglobin Fusion Polypeptide HpNC

<400> SEQUENCE: 61

Asp Ser Gly Asn Asp Val Thr Asp Ile Ala Asp Asp Gly Gly Ser Gly
1 5 10 15

Gly Arg His Tyr Glu Gly Ser Thr Val Pro Glu Lys Lys Thr Pro Lys
20 25 30

Ser Gly Gly
35

<210> SEQ ID NO 62
<211> LENGTH: 49
<212> TYPE: DNA
<213> ORGANISM: Artificial Sequenece
<220> FEATURE:
<223> OTHER INFORMATION: Forward primer RI-F1 for Human Haptoglobin fusion polypeptide HpNC

<400> SEQUENCE: 62
agaattctga tagcggcaac gatgtgaccg atattgcgga tgatggtgg 49

<210> SEQ ID NO 63
<211> LENGTH: 44
<212> TYPE: DNA
<213> ORGANISM: Artificial Sequenece
<220> FEATURE:
<223> OTHER INFORMATION: Forward primer F2 for Human Haptoglobin fusion polypeptide HpNC

<400> SEQUENCE: 63
tgaccgatat tgcggatgat ggtggtagtg gtggtcgtca ttat 44

<210> SEQ ID NO 64
<211> LENGTH: 41
<212> TYPE: DNA
<213> ORGANISM: Artificial Sequenece
<220> FEATURE:
<223> OTHER INFORMATION: Forward primer F3 for Human Haptoglobin fusion polypeptide HpNC

<400> SEQUENCE: 64

-continued

```
atggtggtag tggtggtcgt cattatgaag gtagcaccgt t                        41


<210> SEQ ID NO 65
<211> LENGTH: 47
<212> TYPE: DNA
<213> ORGANISM: Artificial Sequenece
<220> FEATURE:
<223> OTHER INFORMATION: Reverse primer R2 for Human Haptoglobin fusion
      polypeptide HpNC

<400> SEQUENCE: 65

ggttttcttc tccggaacgg tgctaccttc ataatgacga ccaccac                  47


<210> SEQ ID NO 66
<211> LENGTH: 47
<212> TYPE: DNA
<213> ORGANISM: Artificial Sequenece
<220> FEATURE:
<223> OTHER INFORMATION: Reverse primer Xho-R1 for Human Haptoglobin
      fusion polypeptide HpNC

<400> SEQUENCE: 66

tctcgagacc accgctcttt ggggttttct tctccggaac ggtgcta                  47


<210> SEQ ID NO 67
<211> LENGTH: 99
<212> TYPE: DNA
<213> ORGANISM: Oryctolagus cuniculus
<220> FEATURE:
<223> OTHER INFORMATION: cDNA encoding rabbit Neutrophile peptide-1 (NP-1)

<400> SEQUENCE: 67

gtggtctgtg cgtgcagacg agccctctgt ttgcctcggg aacgtcgtgc tgggttctgc     60

agaatccgtg gaagaatcca cccactctgc tgccgccgc                           99


<210> SEQ ID NO 68
<211> LENGTH: 33
<212> TYPE: PRT
<213> ORGANISM: Oryctolagus cuniculus
<220> FEATURE:
<223> OTHER INFORMATION: rabbit Neutrophile peptide-1 (NP-1)

<400> SEQUENCE: 68

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
20                  25                  30

Arg
```

What is claimed is:

1. A chimeric gene comprising:

a. a first DNA sequence encoding a protein transduction domain (PTD) having HIV-Tat PTD activity;

b. a second DNA sequence, linked in translation frame with the first DNA sequence, a encoding J-domain having a heat shock protein 70 (Hsp70)-interacting activity; and c. a third DNA sequence, linked in translation frame with the second DNA sequence, a target protein or polypeptide.

2. The chimeric gene of claim 1, wherein the first DNA sequence encodes a protein transduction domain (PTD) comprising the amino acid sequence set forth by SEQ ID NO: 1.

3. The chimeric gene of claim 1, wherein the second DNA sequence encodes a J-domain comprising the amino acid sequence encoding set forth by SEQ ID NO: 3.

4. The chimeric gene of claim 1, wherein the first DNA sequence encodes a protein transduction domain (PTD) comprising the amino acid sequence set forth by SEQ ID NO: 1, and the second DNA sequence encodes a J-domain comprising the amino acid sequence set forth by SEQ ID NO: 3.

5. The chimeric gene of claim 1, wherein the J-domain is a member selected from the group consisting of a heat shock protein 40 (Hsp40) J-domain and a simian virus 40 (SV40) large T antigen (Tag) J-domain.

6. The chimeric gene of claim 1, wherein the J-domain is from a human heat shock protein 40.

7. A protein expression vector comprising the chimeric gene of claim 1.

8. A protein expression vector comprising the chimeric gene of claim 4.

9. A protein expression vector comprising the chimeric gene of claim 5.

10. A protein expression vector comprising the chimeric gene of claim 2.

11. A protein expression vector comprising the chimeric gene of claim 3.

12. A protein expression vector comprising the chimeric gene of claim 6.

13. An isolated host cell comprising the expression vector of claim 7.

14. An isolated host cell comprising the expression vector of claim 8.

15. An isolated host cell comprising the expression vector of claim 9.

16. An isolated host cell comprising the expression vector of claim 10.

17. The host cell of claim 13, wherein the host cell is an *E. coli* cell.

18. A method for enhancing immunogenicity and/or solubility of a target protein or polypeptide in a host cell expression system comprising the steps of:

a. generating a protein expression vector according to claim 7;

b. transfecting a host cell with the expression vector;

c. culturing the host cell transfected with the expression vector under conditions that permit expression of the target protein or polypeptide; and d. lysing the host cell to release proteins or polypeptides;

e. separating soluble from insoluble proteins or polypeptides; and f. isolating the soluble target proteins or polypeptides, wherein the yield of the soluble inherently more immunogenic target proteins or polypeptides is significantly greater that that from an expression vector without PTD and J-domain.

19. A method of expressing a target protein or polypeptide comprising the steps of:

a. transfecting a host cell with the expression vector of claim 7;

b. culturing the host cell transfected with the expression vector under conditions that permit expression of the target protein or polypeptide; and c. isolating the target protein or polypeptide.

20. An isolated host cell comprising the expression vector of claim 11.

* * * * *

UNITED STATES PATENT AND TRADEMARK OFFICE

CERTIFICATE OF CORRECTION

PATENT NO. : 7,524,648 B2
APPLICATION NO. : 12/149606
DATED : April 28, 2009
INVENTOR(S) : Ming-Yu Chen et al.

It is certified that error appears in the above-identified patent and that said Letters Patent is hereby corrected as shown below:

On the Title Page, Item (56), Column 2, line 5, delete “antigenswith” and substitute --antigens with--

Column 7, Line 23, delete “pET22b-PTD1, pET22b-PTD1-J1, and pET22b-PTD1-target” and substitute --pET22b-PTD1, pET22b-PTD1-J1, and pET22b-PTD1-J1-target--

Column 47, Line 60, delete “a encoding J-domain” and substitute --encoding J-domain--

Signed and Sealed this

Tenth Day of November, 2009

David J. Kappos
*Director of the United States Patent and Trademark Office*

UNITED STATES PATENT AND TRADEMARK OFFICE

CERTIFICATE OF CORRECTION

PATENT NO. : 7,524,648 B2
APPLICATION NO. : 12/149606
DATED : April 28, 2009
INVENTOR(S) : Ming-Yu Chen et al.

It is certified that error appears in the above-identified patent and that said Letters Patent is hereby corrected as shown below:

On the Title Page, Item (74), line 2, delete "Hsin-Ming Saunders" and substitute --Hsiu-Ming Saunders--.

Signed and Sealed this

Twenty-fourth Day of November, 2009

David J. Kappos

David J. Kappos
*Director of the United States Patent and Trademark Office*

UNITED STATES PATENT AND TRADEMARK OFFICE

CERTIFICATE OF CORRECTION

PATENT NO. : 7,524,648 B2
APPLICATION NO. : 12/149606
DATED : April 28, 2009
INVENTOR(S) : Ming-Yu Chen et al.

It is certified that error appears in the above-identified patent and that said Letters Patent is hereby corrected as shown below:

In the drawing, Sheet 2 of 15, consisting of FIG. 2A, should be replaced with the corrected FIG. 2A as shown on the attached Sheet 2 of 15.

In the drawing, Sheet 3 of 15, consisting of FIG. 2B, should be replaced with the corrected FIG. 2B as shown on the attached Sheet 3 of 15.

Cols. 21 and 23;
In the SEQUENCE LISTING, SEQ ID NOs: 3 and 4 should be replaced with the corrected SEQ ID NOs: 3 and 4 as shown on the attached pages.

Signed and Sealed this

Eighth Day of June, 2010

David J. Kappos
*Director of the United States Patent and Trademark Office* pET-22b-PTD$_1$

T7 primer
AGATCT CGATCCCCGCGAAAT TAATACGACTCACTAT AGG GGAATTGTGAGCGGATAACAATTCC CC TCTAGA AATAATTTTGTTTAACTTTAA
*Bgl*II T7 promoter lac operator *Xba*I

*Nde*I
CTTTAAGAAGGAG ATATA CAT ATG TAT GGT CGT AAG AAA CGT CGT CAG CGT CGT CGT GTG
rbs Met Tyr Gly Arg Lys Lys Arg Arg Gln Arg Arg Arg Val

*Bam*HI *Eco*RI *Sac*I *Sal*I *Hind*III *Not*I *Xho*I
GGG ATC CG AAT TCG AGC TCC GTC GAC AAG CTT GCG GCC GCA CTC GAG
Gly Ile Asn Ser Ser Ser Val Asp Lys Leu Ala Ala Ala Leu Glu CAC CAC CAC CAC CAC CAC TGA GATCCGGCTGCTAACAAAGCCCGAAAGGAAGCTGAGTTGGCTGCTGCCACCGCTGAGCAATAA
His His His His His His stop
His-tag

CTAGCATAACCCCTTGGGGCCTCTAAACGGGTCTTGAGGGGTTTTTTG
T7 terminator

FIG. 2A pET-22b-PTD$_1$-J$_1$

```
                         T7 primer
                         -------------------->
AGATCT CGATCCCCGCGAAAT TAATACGACTCACTAT AGG GGAATTGTGAGCGGATAACAATTCC CC TCTAGA AATAATTTTGTTTAACTTTAA
BglII                    T7 promoter            lac operator              XbaI

                        NdeI
CTTTAAGAAGGAG ATATA CAT ATG TAT GGT CGT AAG AAA CGT CGT CAG CGT CGT CGT GTG
      rbs                   Met Tyr Gly Arg Lys Lys Arg Arg Gln Arg Arg Arg Val

BamHI
GGG ATC CTG GGT AAA GAT TAC TAC CAG ACT CAC GGT CTC GCT CGT GGT GCA TCT GAT GAT GAA ATC AAA CGT GCT TAC CGT CGT CAG GCA CTG CGT TAC
Gly Ile Leu Gly Lys Asp Tyr Tyr Gln Thr His Gly Leu Ala Arg Gly Ala Ser Asp Asp Glu Ile Lys Arg Ala Tyr Arg Arg Gln Ala Leu Arg Tyr

CAT CCA GAC AAA AAC AAA GAA CCG CGT GCA GAA GAG AAA TTC AAA GAG ATC GCA GAA GCA TAC GAC GTT CTG AGC GAT CCA CGT AAA CGT GAA ATC TTC
His Pro Asp Lys Asn Lys Glu Pro Arg Ala Glu Glu Lys Phe Lys Glu Ile Ala Glu Ala Tyr Asp Val Leu Ser Asp Pro Arg Lys Arg Glu Ile Phe

GAC CGT TAC GGT GAA GAA GGT CTG AAA GGT GGT TCT GGT GGT GC
Asp Arg Tyr Gly Glu Glu Gly Leu Lys Gly Gly Ser Gly Gly Ala

 EcoRI   SacI     SalI  HindIII   NotI     XhoI
G AAT TCG AGC TCC GTC GAC AAG CTT GCG GCC GCA CTC GAG
  Asn Ser Ser Ser Val Asp Lys Leu Ala Ala Ala Leu Glu

CAC CAC CAC CAC CAC CAC TGA GATCCGGCTGCTAACAAAGCCCGAAAGGAAGCTGAGTTGGCTGCTGCCACCGCTGAGCAATAA
His His His His His His stop
         His-tag

CTAGCATAACCCCTTGGGGCCTCTAAACGGGTCTTGAGGGGTTTTTTG
                T7 terminator
```

FIG. 2B

<210> 3
<211> 72
<212> PRT
<213> Homo sapiens

<400> 3

Gly Lys Asp Tyr Tyr Gln Thr His Gly Leu Ala Arg Gly Ala Ser Asp
1 5 10 15

Asp Glu Ile Lys Arg Ala Tyr Arg Arg Gln Ala Leu Arg Tyr His Pro
20 25 30

Asp Lys Asn Lys Glu Pro Arg Ala Glu Glu Lys Phe Lys Glu Ile Ala
35 40 45

Glu Ala Tyr Asp Val Leu Ser Asp Pro Arg Lys Arg Glu Ile Phe Asp
50 55 60

Arg Tyr Gly Glu Glu Gly Leu Lys
65 70

<210> 4
<211> 216
<212> DNA
<213> Artificial Sequenece

<220>
<223> HSP40 J-domain (J1)-encoding sequence

<400> 4
ggtaaagatt actaccagac tcacggtctc gctcgtggtg catctgatga tgaaatcaaa 60
cgtgcttacc gtcgtcaggc actgcgttac catccagaca aaaacaaaga accgcgtgca 120
gaagagaaat tcaaagagat cgcagaagca tacgacgttc tgagcgatcc acgtaaacgt 180
gaaatcttcg accgttacgg tgaagaaggt ctgaaa 216

UNITED STATES PATENT AND TRADEMARK OFFICE

CERTIFICATE OF CORRECTION

PATENT NO. : 7,524,648 B2
APPLICATION NO. : 12/149606
DATED : April 28, 2009
INVENTOR(S) : Ming-Yu Chen et al.

It is certified that error appears in the above-identified patent and that said Letters Patent is hereby corrected as shown below:

Title Page;

In Section (56) References Cited:

In the Foreign Patent Documents please insert the following:

-- WO 96/033738 10/1996 Volvovitz, Franklin --

Signed and Sealed this
Twelfth Day of April, 2011

David J. Kappos
*Director of the United States Patent and Trademark Office*